US008187329B2

(12) United States Patent
Theofilos

(10) Patent No.: US 8,187,329 B2
(45) Date of Patent: May 29, 2012

(54) INTERBODY FUSION SYSTEM WITH INTERVERTEBRAL IMPLANT RETENTION ASSEMBLY

(75) Inventor: Charles S. Theofilos, Palm Beach Gardens, FL (US)

(73) Assignee: Spartan Cage Holding, LLC, Palm Beach Gardens, FL (US)

( * ) Notice: Subject to any disclaimer, the term of this patent is extended or adjusted under 35 U.S.C. 154(b) by 161 days.

(21) Appl. No.: 12/710,103

(22) Filed: Feb. 22, 2010

(65) Prior Publication Data
US 2010/0217393 A1 Aug. 26, 2010

Related U.S. Application Data

(60) Provisional application No. 61/154,038, filed on Feb. 20, 2009, provisional application No. 61/239,230, filed on Sep. 2, 2009.

(51) Int. Cl.
*A61F 2/44* (2006.01)
(52) U.S. Cl. .................................... 623/17.11
(58) Field of Classification Search .... 623/17.11–17.16; 606/246, 248, 301–306, 247
See application file for complete search history.

(56) References Cited

U.S. PATENT DOCUMENTS

| | | | |
|---|---|---|---|
| 28,841 A | 6/1976 | Allgower et al. |
| 4,955,908 A | 9/1990 | Frey et al. |
| 5,372,598 A | 12/1994 | Luhr et al. |
| 5,458,642 A | 10/1995 | Beer et al. |
| 5,545,164 A | 8/1996 | Howland |
| 5,549,612 A | 8/1996 | Yapp et al. |
| 5,616,142 A | 4/1997 | Yuan et al. |
| 5,620,443 A | 4/1997 | Gertzbein et al. |
| 5,702,395 A | 12/1997 | Hopf |
| 5,888,223 A | 3/1999 | Bray, Jr. |
| 6,004,353 A | 12/1999 | Masini |
| 6,017,345 A | 1/2000 | Richelsoph |

(Continued)

FOREIGN PATENT DOCUMENTS

EP 1417935 A2 5/2004

(Continued)

*Primary Examiner* — Pedro Philogene
(74) *Attorney, Agent, or Firm* — Carter, DeLuca, Farrell & Schmidt, LLP

(57) ABSTRACT

The present disclosure is directed towards a biomechanical implant and anterior, lateral or posterior instrumentation construct. The construct may be of unitary or modular construction, whereby a single molded construction can form the entire assembly, in which case the through holes may be adapted to receive a metallic insert for screw fixation; or alternatively be of a modular construction wherein the anterior/lateral instrumentation and intervertebral spacer are designed for removable locking engagement, one with the other, for insertion by the surgeon as a unitary construct. A unique feature of the construct resides within the instrumentation construction, whereby a single opening formed therein permits two bone screws, or the like fastener device, to be positioned within both the superior and inferior vertebral bodies surrounding the spacer implant, or, for example in the case of a corpectomy or diskectomy with cage insertion, wherein two screws can be fixed within a single vertebral body through a single through hole, and wherein the bone screws are constructed and arranged to cooperate with the retention plate so as to provide locking engagement, one to the other, with the retention plate, upon final fixation thereof. Screw retention elements of alternative shape, based upon the choice of vertical or horizontal orientation, based upon an opened figure eight design, are provided for insertion in a groove formed in the borehole of the instrumentation plate which allows insertion of each fixation element but will prevent a loosened fixation element from falling out of the plate.

33 Claims, 19 Drawing Sheets

U.S. PATENT DOCUMENTS

| | | | |
|---|---|---|---|
| 6,136,002 A | 10/2000 | Shih et al. | |
| 6,193,721 B1 | 2/2001 | Michelson | |
| 6,306,139 B1 | 10/2001 | Fuentes | |
| 6,322,562 B1 | 11/2001 | Wolter | |
| 6,342,074 B1 | 1/2002 | Simpson | |
| 6,355,038 B1 | 3/2002 | Pisharodi | |
| 6,402,756 B1 | 6/2002 | Ralph et al. | |
| 6,432,106 B1 | 8/2002 | Fraser | |
| 6,458,159 B1 | 10/2002 | Thalgott | |
| 6,558,423 B1 | 5/2003 | Michelson | |
| 6,582,468 B1 | 6/2003 | Gauchet | |
| 6,620,163 B1 | 9/2003 | Michelson | |
| 6,629,998 B1 * | 10/2003 | Lin | 623/17.11 |
| 6,652,525 B1 | 11/2003 | Assaker et al. | |
| 6,689,134 B2 | 2/2004 | Ralph et al. | |
| 6,913,607 B2 | 7/2005 | Ainsworth et al. | |
| 6,936,051 B2 | 8/2005 | Michelson | |
| 6,972,019 B2 | 12/2005 | Michelson | |
| 6,984,234 B2 | 1/2006 | Bray | |
| 7,025,769 B1 | 4/2006 | Ferree | |
| 7,033,394 B2 | 4/2006 | Michelson | |
| 7,041,105 B2 | 5/2006 | Michelson | |
| 7,041,135 B2 | 5/2006 | Michelson | |
| 7,077,864 B2 | 7/2006 | Byrd, III et al. | |
| 7,087,057 B2 | 8/2006 | Konieczynski et al. | |
| 7,112,222 B2 | 9/2006 | Fraser et al. | |
| 7,169,150 B2 * | 1/2007 | Shipp et al. | 606/287 |
| 7,172,627 B2 | 2/2007 | Fiere et al. | |
| 7,226,482 B2 | 6/2007 | Messerli et al. | |
| 7,232,441 B2 | 6/2007 | Altarac et al. | |
| 7,232,463 B2 | 6/2007 | Falahee | |
| 7,232,464 B2 | 6/2007 | Mathieu et al. | |
| 7,306,605 B2 | 12/2007 | Ross | |
| 7,326,248 B2 | 2/2008 | Michelson | |
| 7,335,204 B2 | 2/2008 | Tornier | |
| 7,435,262 B2 | 10/2008 | Michelson | |
| 7,442,209 B2 * | 10/2008 | Michelson | 623/17.11 |
| 7,481,811 B2 | 1/2009 | Suh | |
| 7,481,829 B2 | 1/2009 | Baynham et al. | |
| 7,481,830 B2 | 1/2009 | Wall | |
| 7,572,282 B2 | 8/2009 | Boomer et al. | |
| 7,621,942 B2 | 11/2009 | Piehl | |
| 7,625,381 B2 | 12/2009 | Michelson | |
| 7,641,701 B2 | 1/2010 | Kirschman | |
| 7,862,616 B2 * | 1/2011 | Lechmann et al. | 623/17.11 |
| 7,887,591 B2 * | 2/2011 | Aebi et al. | 623/17.15 |
| 7,931,840 B2 * | 4/2011 | Michelson | 264/162 |
| 7,972,363 B2 * | 7/2011 | Moskowitz et al. | 606/246 |
| 7,985,255 B2 * | 7/2011 | Bray et al. | 623/17.11 |
| 2002/0045901 A1 | 4/2002 | Wagner et al. | |
| 2002/0188296 A1 | 12/2002 | Michelson | |
| 2003/0036759 A1 | 2/2003 | Musso | |
| 2003/0060828 A1 | 3/2003 | Michelson | |
| 2003/0130661 A1 | 7/2003 | Osman | |
| 2004/0019353 A1 | 1/2004 | Freid et al. | |
| 2004/0024464 A1 | 2/2004 | Errico et al. | |
| 2004/0126407 A1 | 7/2004 | Falahee | |
| 2004/0199253 A1 | 10/2004 | Link et al. | |
| 2004/0210219 A1 | 10/2004 | Bray | |
| 2005/0071008 A1 | 3/2005 | Kirschman | |
| 2005/0113918 A1 | 5/2005 | Messerli et al. | |
| 2005/0149026 A1 | 7/2005 | Butler et al. | |
| 2005/0177160 A1 | 8/2005 | Baynham et al. | |
| 2005/0187551 A1 | 8/2005 | Orbay et al. | |
| 2005/0234455 A1 | 10/2005 | Binder et al. | |
| 2006/0085071 A1 | 4/2006 | Lechmann et al. | |
| 2006/0106387 A1 | 5/2006 | Fanger et al. | |
| 2006/0247639 A1 | 11/2006 | Anderson | |
| 2007/0219635 A1 | 9/2007 | Mathieu et al. | |
| 2008/0033562 A1 | 2/2008 | Krishna et al. | |
| 2008/0119933 A1 | 5/2008 | Aebi et al. | |
| 2008/0161925 A1 | 7/2008 | Brittan et al. | |
| 2008/0177307 A1 | 7/2008 | Moskowitz et al. | |
| 2008/0183293 A1 | 7/2008 | Parry et al. | |
| 2008/0234681 A1 | 9/2008 | Baynham | |
| 2008/0249569 A1 | 10/2008 | Waugh et al. | |
| 2008/0249575 A1 | 10/2008 | Waugh et al. | |
| 2008/0249625 A1 | 10/2008 | Waugh et al. | |
| 2008/0306596 A1 | 12/2008 | Jones et al. | |
| 2009/0105831 A1 | 4/2009 | Jones et al. | |
| 2009/0162813 A1 | 6/2009 | Glor et al. | |
| 2009/0210062 A1 | 8/2009 | Thalgott et al. | |
| 2009/0264934 A1 | 10/2009 | Youssef et al. | |
| 2010/0087925 A1 | 4/2010 | Kostuik et al. | |
| 2010/0305704 A1 * | 12/2010 | Messerli et al. | 623/17.16 |

FOREIGN PATENT DOCUMENTS

| | | |
|---|---|---|
| EP | 1417935 B1 | 10/2008 |
| WO | WO00/66011 | 11/2000 |
| WO | 2007098288 | 8/2007 |
| WO | WO2007098288 | 8/2007 |
| WO | WO2009064644 | 5/2009 |

* cited by examiner

INTERBODY FUSION SYSTEM WITH INTERVERTEBRAL IMPLANT RETENTION ASSEMBLY

CROSS-REFERENCE TO RELATED APPLICATIONS

This application claims benefit of the filing date of U.S. Provisional Patent Application No. 61/154,038, filed on Feb. 20, 2009, and U.S. Provisional Patent Application No. 61/239,230, filed on Sep. 2, 2009, the contents of each of which is herein incorporated by reference in their entirety.

FIELD OF THE INVENTION

The present invention relates generally to an interbody fusion system having an intervertebral retention assembly, and more particularly to intervertebral implants, and intervertebral implant assemblies incorporating a biomechanical implant construct inclusive of stabilizing instrumentation (an anterior, posterior or lateral stabilizer), constructed and arranged to provide superior and inferior vertebral fixation by multiple fixation elements via a single through hole, which through hole can accommodate a fixation element retainer component (hereinafter referred to as a screw retainer component, e.g. a third piece of instrumentation which acts as a retention device to prevent separation of a loosened fixation element from the stabilizing anterior, posterior or lateral instrumentation.

BACKGROUND OF THE INVENTION

Intervertebral spacer implants, either alone or further provided as an assembly, inclusive of a retention mechanism to help alleviate expulsion and movement of the implant when placed in the spine, are well known. Such implant assemblies are advantageous in providing an implant that is easier to insert in the spine, and which resists expulsion subsequent to implantation. Intervertebral spacer implant assemblies which include a spacer and a plate, where the plate comprises a supplemental or alternative retention mechanism having one or more holes in the anterior end of the plate that are directed toward the superior, inferior or both endplates of adjacent vertebrae are also known in the art. Such implants are used to stabilize and immobilize the spinal segments in the treatment of single or multi-level degenerative disc disease, spinal stenosis, and failed previous fusions, as well as other spine conditions.

The problem with many of these implants resides in preservation of the highest degree of mobility possible, while avoiding backing out or loosening of the implant assembly fastening elements, such as bone screws and the like.

As will be illustrated herein, the prior art devices often lack sufficient means to insure lockable engagement of the anterior instrumentation and fastener elements, nor do they provide passive means to enable screw retention. In many instances the screw retainer components are provided as separate elements, which must be installed by the surgeon via a separate and distinct step subsequent to application of the fixation element.

An additional deficiency of the prior art devices is that they are not designed to enable the surgeon to place multiple bone fasteners within a single entry point, so as to provide the surgeon with the freedom to moderate the angularity of the fastener elements in such a manner that they can be targeted for both the superior and inferior vertebral bodies surrounding the implant.

The instant invention satisfies a long felt need in the art by providing a biomechanical implant with stabilizing instrumentation, (which instrumentation will alternatively be referred to as anterior, posterior or lateral instrumentation throughout the present disclosure) which provides stabilization to the adjacent vertebra wherein a single opening in such instrumentation permits bone screws or equivalent fixation elements to be positioned within both the superior and inferior vertebral body surrounding the implant, and wherein said bone screws or equivalent fixation elements are constructed and arranged to cooperate with an elongated and dished curvilinear opening formed within a first surface of the anterior instrumentation, effective to urge the fixation elements into locking engagement, one to the other, as well as with the anterior instrumentation, upon final fixation of the components, thereby forming a frictionally engaged assemblage. A further long felt need is met by the inclusion of a screw retainer component, which is in the form of a passive locking ring or equivalent device, which constitutes a third piece of instrumentation in this device. The screw retainer component resides in a mounting area formed near the first surface of the anterior instrumentation and is constructed and arranged to deflect from a resting position, so as to allow passage of each fastener element, subsequent to which passage, the screw retainer component returns to its initial position so as to block any of the fasteners from separating from the anterior instrumentation, should loosening or breakage occur.

DESCRIPTION OF THE PRIOR ART

U.S. Pat. No. 7,041,135 (Michelson) is directed toward an apparatus including an interbody spinal fusion implant having a leading end, a trailing end, and a length therebetween, and opposed upper and lower portions adapted to contact each of the adjacent vertebral bodies. Each of the upper and lower portions has at least one screw hole passing there through proximate the trailing end. The apparatus further includes bone screws adapted for placement through the screw holes of the upper and lower portions and into each of the adjacent vertebral bodies adjacent the disc space to be fused and into which the implant is adapted to be positioned. Although an embodiment is shown containing a single recess opening having two exit holes, so that two screws are sited in the same aperture, the screws can not impinge upon each other to create a frictional locking engagement with the plate, and therefore, at least one lock is taught to prevent the bone screws from backing out of the vertebral bodies and implant, the necessity of which is eliminated by the instantly disclosed invention.

U.S. Published Patent Application 2005/0071008 (Kirschman) relates to a spinal fusion system and method for use as a prosthetic implant. The system and method includes a housing dimensioned to be situated between adjacent spinal bones, such as adjacent vertebrae. The housing cooperates with the spinal bones to define a graft area for receiving graft material, which may be inserted anteriorly into the housing during a surgical operation such as a vertebrectomy or discectomy. A housing may have various features such as migration preventers to prevent the housing from migrating posteriorly towards a spinal column and can be used with a cover that permits the housing to "float" relative thereto. Screws are provided in one embodiment and are dimensioned or configured to lock against each other to retain the screws and, consequently, the cover in place. The publication fails to teach or suggest a construction wherein a single opening permits a bone screw to be positioned within both the superior and inferior vertebral body surrounding the implant, or wherein two bone screws or the like are positionable through a single hole within a particular vertebral body, and wherein said bone screws or the like are in locking engagement with the intervertebral implant assembly.

U.S. Published Patent Application 2005/0187551 (Orbay et al) is directed toward a bone plating system which includes a plate, fixed angle and variable angle bone screws, and corresponding set screws for each type of the bone screws. The plate includes common openings adapted to receive the variable and fixed angle bone screws, both of which can be locked relative to the plate with the set screws. In all modes of use, a set screw, sometimes in combination with a sliding washer, is then used to fix the level of compression and prevent loosening. In one mode of use, a bone screw can also be driven to cause displacement of the plate such that pressure is applied to maintain bone parts together about a fracture in tight engagement. It is noted that in FIG. 15, screw head 775 locks down on adjacent screw head 161, and that FIG. 3 teaches an oval opening into which the screws are inserted. Again, the publication fails to teach or suggest a construction wherein a single opening permits a bone screw to be positioned within both the superior and inferior vertebral body surrounding the implant, or wherein two bone screws or the like are positionable through a single hole within a particular vertebral body, and wherein said bone screws or the like are in locking engagement with the intervertebral implant assembly.

WO 2007098288 (Messerli et al) shows an implant with anterior plate means to affix the bone spacer by means of screws directed both inferiorly and superiorly of the anterior plate. This device does not include an oval hole receiving two screws but rather has separate screw holes directed upwardly and downwardly. See FIGS. 2, 3 and 5 as exemplary thereof. This publication also fails to teach or suggest a construction wherein a single opening permits a bone screw to be positioned within both the superior and inferior vertebral body surrounding the implant, or wherein two bone screws or the like are positionable through a single hole within a particular vertebral body, and wherein said bone screws or the like are in locking engagement with the intervertebral implant assembly.

U.S. Published Patent Application 2006/0085071 (Lechmann) teaches an intervertebral implant having a three-dimensional body (10) and a securing plate (1). The three-dimensional body (10) includes an upper side (1) and an underside (2) which are suitable for abutting the end plates of two adjacent vertebral bodies, a left side surface (3) and a right side surface (4), a front surface (5) and a rear surface (6), a horizontal middle plane (7) between the upper side (1) and the underside (2), and a vertical middle plane (12) extending from the front surface (5) to the rear surface (6). The three-dimensional body further includes a plurality of boreholes (9a) passing through the body (10), which are suitable for accommodating longitudinal fixation elements (20). The intervertebral implant also includes a front plate (8) displaceably disposed as an insert with the front side (5) of the three-dimensional body, the front plate (8) having a plurality of boreholes (9) in which the longitudinal fixation elements (20) can be anchored, and whose openings overlap with the openings of the boreholes of the three-dimensional body (10). A securing plate can be fastened essentially parallel to the front plate (8) at the three-dimensional body (10) in such a manner that the boreholes of the front plate (9) are covered at least partly by the securing plate (18). By virtue of the configuration of the intervertebral implant, a rigid, firm connection between the intervertebral implant and the longitudinal fixation elements used to fasten it, is possible. This publication likewise fails to teach or suggest a construction wherein a single opening permits a bone screw to be positioned within both the superior and inferior vertebral body surrounding the implant, or wherein two bone screws or the like are positionable through a single hole within a particular vertebral body, and wherein said bone screws or the like are in locking engagement with the intervertebral implant assembly. On the contrary, the reference requires the use of a secondary locking plate in order to prevent backing out or loosening of the bone screws.

U.S. Reissue 28,841 (Allgower et al) and U.S. Published Patent Application 2002/0045901 (Wagner) are exemplary of bone plates having an oval screw opening. They disclose a bone plate which includes an upper surface, a bone contacting surface, and at least one hole extending through the upper and bone contacting surfaces. The bone plate defines a longitudinal axis. The at least one hole defines a central axis and is elongated in a direction substantially aligned with the longitudinal axis. The hole may include a threaded portion and a non-threaded portion, and the threaded portion may extend through an angle of between about 190° and about 280° with respect to the central axis.

U.S. Published Patent Application 2006/0247639 (Anderson) shows dual screw holes connected by a slot, and in one embodiment (FIG. 10) illustrates divergent screw holes.

The prior art fails to provide a construction wherein a single opening permits bone screws to be positioned within both the superior and inferior vertebral body surrounding the implant, or wherein two bone screws or the like are positionable through a single hole within a particular vertebral body, and wherein said bone screws or the like are in locking engagement with the intervertebral implant assembly, upon final fixation thereof.

SUMMARY OF THE INVENTION

The present invention is directed towards an integratable biomechanical implant construct comprising plural components inclusive of 1) a biomechanical spacer implant for insertion within an intervertebral space, 2) an anterior, posterior or lateral instrumentation component effective for vertebral body fixation and maintenance of the biomechanical spacer implant within the intervertebral space, and 3) a plurality of fastener components effective for securing the biomechanical implant construct to the vertebral bodies. The biomechanical spacer implant and anterior instrumentation component are designed for removable locking engagement, one with the other, for insertion by the surgeon as a unitary construct. It is contemplated that the biomechanical implant construct may be of either a unitary or a modular construction. When a unitary construction is provided, a single molded construction, e.g. of PEEK, titanium, or the like, can form the entire construct. In the case where the unitary construct is formed from a polymeric material, the through holes formed within the anterior instrumentation component may be reinforced for retention of the screw retainer components by incorporation of a metallic insert to make possible the novel anterior instrumentation/fastener component locking feature specific to the present invention.

A unique feature of the construct resides within the anterior instrumentation construction, whereby a single opening formed within the anterior instrumentation permits two bone screws, or the like fastener elements, to be positioned within both the superior and inferior vertebral bodies surrounding the spacer implant or, for example in the case of a corpectomy or diskectomy with cage insertion, wherein two screws can be fixed within a single vertebral body through a single through hole, and wherein the bone screws are constructed and arranged to cooperate with the anterior instrumentation so as to provide locking engagement, one to the other, with the anterior instrumentation, upon final fixation thereof. The use of a single screw hole allows the use of a relatively smaller faceplate than is possible with prior art designs, thus providing a more compact device which decreases the profile of the implant and concomitantly results in a decrease in esophageal compression.

Alternative embodiments are illustrated inclusive of a horizontal spaced orientation and a vertical spaced orientation. In the horizontal spaced orientation the screws are aligned side-by-side with alternate screws targeting the superior and inferior vertebral bodies respectively. In the vertical spaced orientation, the screws are stacked one above the other to allow for a more compact footprint, and again alternate between the superior and inferior vertebral bodies. Common to all embodiments is a borehole or through-hole assembly, which includes arcuate and dished curvilinear sidewalls. These sidewalls are designed to cooperate with the curved faces of the screwheads to urge the screwheads into a convergent relationship with one another and with the borehole assembly, whereby the act of tightening the bone screws within the common borehole assembly forces the screwheads and borehole assembly into locking engagement with one another when fully seated.

As an additional safety feature to guard against screw separation in the event of accidental backing out or breakage of the screws, a unique screw retainer component is further provided. The screw retainer component comprises an "open eight" retention clip within an area of the anterior instrumentation designed to receive it. In the horizontal spaced orientation the screw retainer component is illustrated as being in the form of a planar retention clip, while in the vertical spaced orientation, the clip is bent to conform to the internal shape of the anterior instrumentation access hole. In both cases, the screw retainer component is designed to deflect during insertion of each screw, and then return to its original position to prevent a loosened or broken screw from falling out of the anterior instrumentation.

The implant of the present invention preferably may be inserted using a one-step implantation process, as compared to a two-step process. Furthermore, the aspect is minimized due to the novel construction of the retention plate portion, thereby permitting the inferior and superior bone fixation to be essentially coplanar, thus eliminating the exacerbation of instability that may be caused by off-center loading resulting from the placement of multiple fasteners about areas of flexion or extension. The use of minimal aspect fixation should further minimize irritation of soft tissue, while providing improved segmental stability in flexion, extension and rotation.

Accordingly, it is an objective of the instant invention to provide a biomechanical implant and anterior instrumentation construct comprised of an intervertebral implant and a retention member which are constructed and arranged to form a permanent, rigid connection with bone fixation elements, so that, even if the bone structure is weakened, there is no loosening between the anterior instrumentation and the bone fixation elements. Moreover, the construct with biomechanical implant (stabilizer) enables superior and inferior vertebral fixation by multiple bone fixation elements via a single through hole, such that, upon fixation to the bony elements, said multiple fixation elements are in frictional engagement with each other and with the implant retention member, whereby all bone fixation elements are secured simultaneously.

It is an additional objective of the instant invention to provide a screw retainer component to guard against escape of a dislodged screw from the device.

It is a further objective of the instant invention to provide an intervertebral biomechanical implant and anterior instrumentation construct suitable for insertion by either an anterior, posterior or lateral surgical approach.

It is yet an additional objective of the instant invention to provide an alternative embodiment which will further enhance the frictional engagement and locking characteristics of the present invention by modifying the instantly disclosed anterior instrumentation and bone fastener elements to utilize elements of the TIFIX® locking technology, in accordance with the teaching of U.S. Pat. No. 6,322,562, the contents of which is herein incorporated by reference, whereby each screw head forms an autogenic lock to the plate upon insertion.

The present invention accomplishes the objectives set out above by providing a biomechanical implant and anterior instrumentation construct, comprising a three-dimensional body having an upper side and an under side which are suitable for abutting the end plates of two adjacent vertebral bodies. The three-dimensional body further includes a left side surface and a right side surface, a front surface and a rear surface, a horizontal middle plane between the upper side and the under side, and a vertical middle plane extending from the front surface to the rear surface. The intervertebral implant assembly further includes a construct inclusive of a biomechanical implant and anterior instrumentation which may form a unitary construct inclusive of the implant or be designed for removable engagement with the three-dimensional intervertebral implant body, wherein the retention member includes a plurality of boreholes, each of said boreholes designed for reception of at least two bone fixation elements, positionable in the superior and inferior vertebral bodies adjacent the intervertebral implant, such that, upon fixation to the bony elements, said multiple fixation elements are in frictional engagement with each other and with the implant retention member, whereby all bone fixation elements are secured simultaneously.

Other objects and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

DETAILED DESCRIPTION OF THE INVENTION

Figure 1:
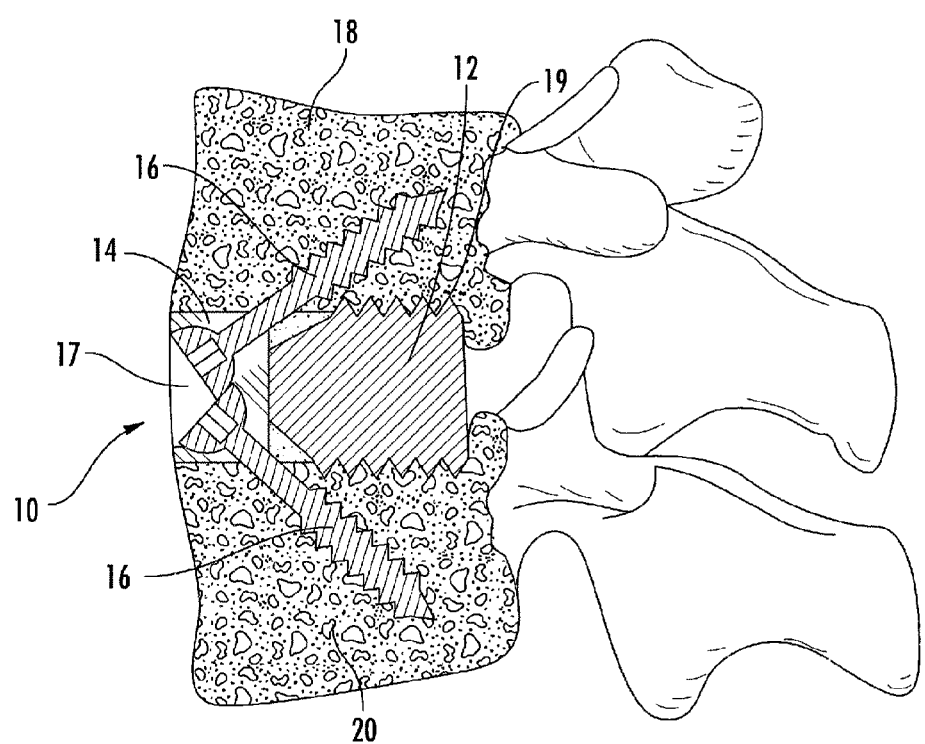
FIG. 1 illustrates a cross-sectional view of a biomechanical implant construct, in accordance with the instant invention, inserted within the intervertebral space, and fixated to both the superior and inferior vertebral bodies adjacent thereto.

Now referring to FIG. 1, the intervertebral implant assembly, generally referred to by numeral 10, includes an implant member 12, and a retention member 14, illustrated as, albeit not limited to, a bone plate. Both plate 14 and implant 12 may be formed of PEEK (poly(ether ether ketone)), titanium, titanium alloy, stainless steel, allograft bone or any other suitable, biocompatible material. It is contemplated that implant 12 may be formed of bone, or an artificial material other than bone which may be harder and/or stronger than bone, such as plastic or ceramic materials. It is further contemplated that the implant material will have the same, more or less elasticity than bone. The implant 12 may include, or be treated with, a bone growth promoting material such as, but not limited to, bone morphogenic protein, hydroxyapatite, and genes coding for the production of bone. Implant 12 may be a source for osteogenesis, be at least in part bioabsorbable, and be treated with, or applied in conjunction with a substance, as known in the art, to inhibit scar formation and/or promote fusion of the bones. Preferably retention member 14 is formed of metal or metal alloy and the spacer is formed of PEEK or other polymer, or alternatively bone or ceramic or radiolucent biocompatible material. Bone fixation elements 16, illustrated, albeit not limited to bone screws, may be formed of titanium, titanium alloy or stainless steel. The bone fixation elements 16 may be in the form of a screw, a staple or nail, a fluted cannulated screw or nail with collapsible/deployable spurs which are deployed and thereby embedded within the bone upon insertion of a secondary nail or screw within the cannulated space, or similar functionally equivalent elements. Furthermore, the implant 12 may include one or more openings (FIG. 3B, 42) designed to receive bone graft material. Subsequent to insertion of the intervertebral implant assembly 10 within the intervertebral space, bone fixation elements, e.g. screws 16, are driven into the inferior 20 and superior 18 adjacent vertebral bodies, via access through hole 17. Upon being fixated within said access hole 17, the elements 16 are urged into locking engagement with the curvilinear seat of anterior instrumentation retention member 14, and each other, so as to reduce or eliminate the possibility of loosening. Due to the single access hole design, the screws essentially reside in a single plane common to the superior and inferior vertebral bodies, and have adjustable angularity at the surgeon's discretion.

It is contemplated by the invention that the access through hole 17 may include a single exit aperture or dual diverging exit apertures. The seat of each aperture, whether integral with the assembly, or formed within a metallic insert which is subsequently inserted into the assembly, may include a spherical or semi-spherical dished and curvilinear seat for each fastener. This feature will provide for variation in screw trajectory and increased face contact between the fixation elements and the plate or seat. In a preferred albeit non-limiting embodiment, the fastener will be formed with a spherical or semi-spherical head with a substantially flat upper surface. Such construction will allow the spherical surface of the second fastener, e.g. screw, to engage the top surface of the first screw regardless of trajectory of both screws. Such construction insures repeatable and reliable head-to-head contact independent of fastener trajectories.

In a particular embodiment of this invention the stabilizing bone plate useful in an interbody fusion system for stabilizing a biomechanical spinal implant will be comprised of a bone plate having a left side surface and a right side surface, a top surface and a bottom surface, a first upper surface and a second lower surface, with a distance between said first upper surface and said second lower surface defining a thickness of said plate, a horizontal middle plane between the first upper surface and the second lower surface and a plurality of boreholes suitable for accommodating longitudinal fixation elements extending through said thickness of said plate, wherein each of said boreholes has an elongated slot located at or near said horizontal middle plane, and surrounded by arcuate and dished curvilinear sidewalls which form an engagement seat extending from said elongated slot to said first upper surface for receiving at least two bone fixation elements therein, each of said bone fixation elements having a screw head adapted to engage or be engaged by an engaging surface of each screw head to urge the screw heads into a convergent and interference relationship with one another and with said engagement seat upon tightening, thereby resulting in a locking engagement of said bone plate engagement seat and said fixation elements and a diverging outlet portion extending from said elongated slot toward said second lower surface, said divergent outlet being adapted to provide a range of angulation of each said fixation elements, whereby each of said fixation elements is individually positionable within both an inferior and superior vertebral body associated with said interbody fusion system.

Figure 2A:
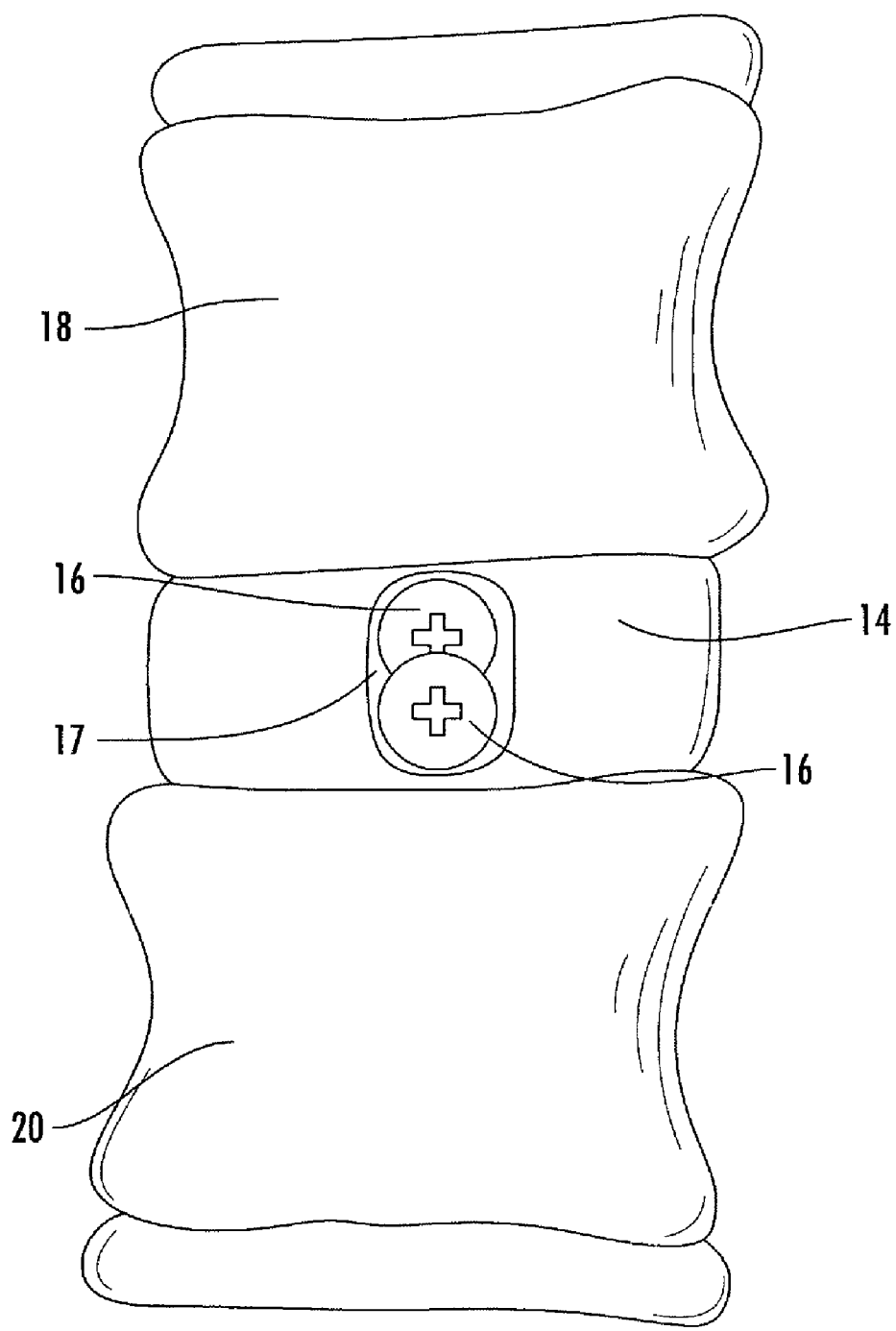
FIG. 2A illustrates a top-view of a biomechanical implant construct as positioned in FIG. 1, illustrating the bone fixation elements positioned in the adjacent superior and inferior vertebral bodies, and in locking engagement with the retention member.
Figure 2B:
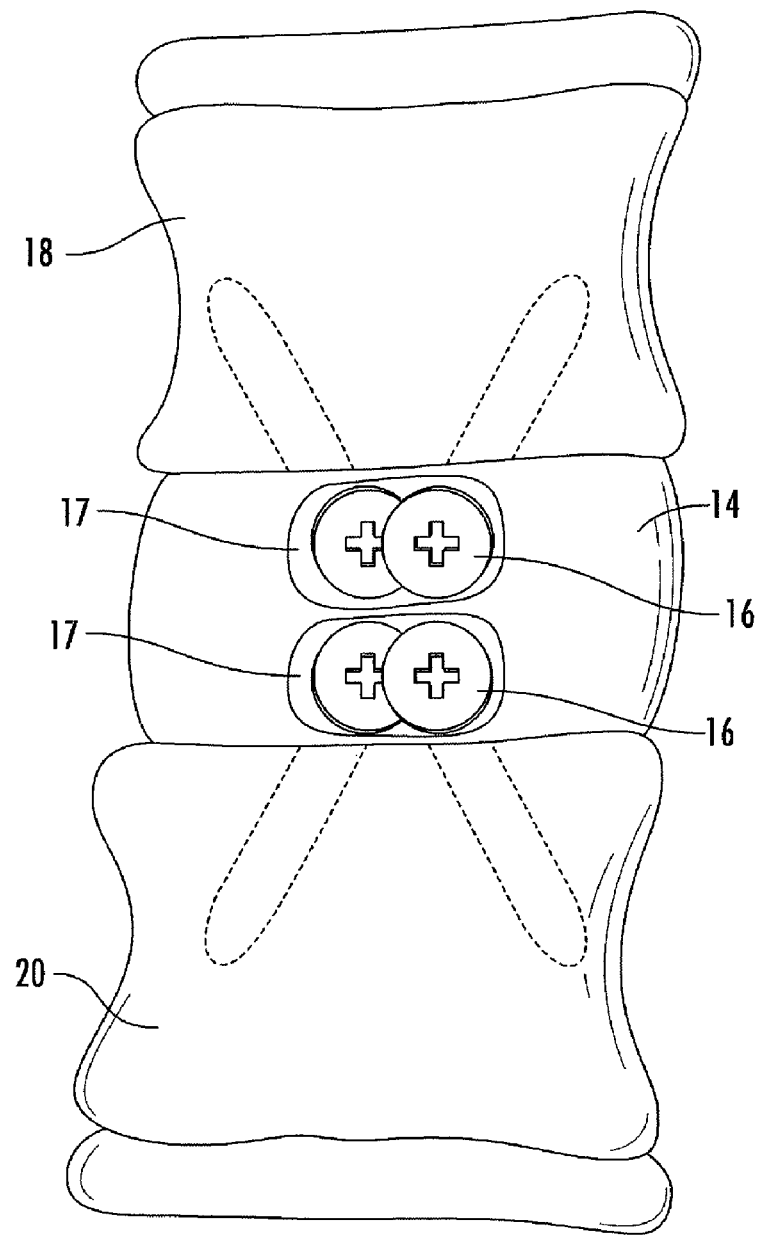
FIG. 2B illustrates a top-view of a biomechanical implant construct as positioned in FIG. 1, illustrating through holes positioned so as to enable two bone fixation elements to be separately positioned within one or both of the adjacent superior or inferior vertebral bodies, and in locking engagement with the retention member.

Now referring to FIG. 2A, the interlocking frictional engagement of the elements 16 and retention member 14 are further illustrated as they reside in through hole 17. Alternatively, as illustrated in FIG. 2B, the through hole(s) 17 may be formed so as to enable two bone fixation elements 16 to be deployed through a single through hole 17, and to be separately positioned within one or both of the adjacent superior or inferior vertebral bodies, and in locking engagement with the retention member 14.

Figure 3A:
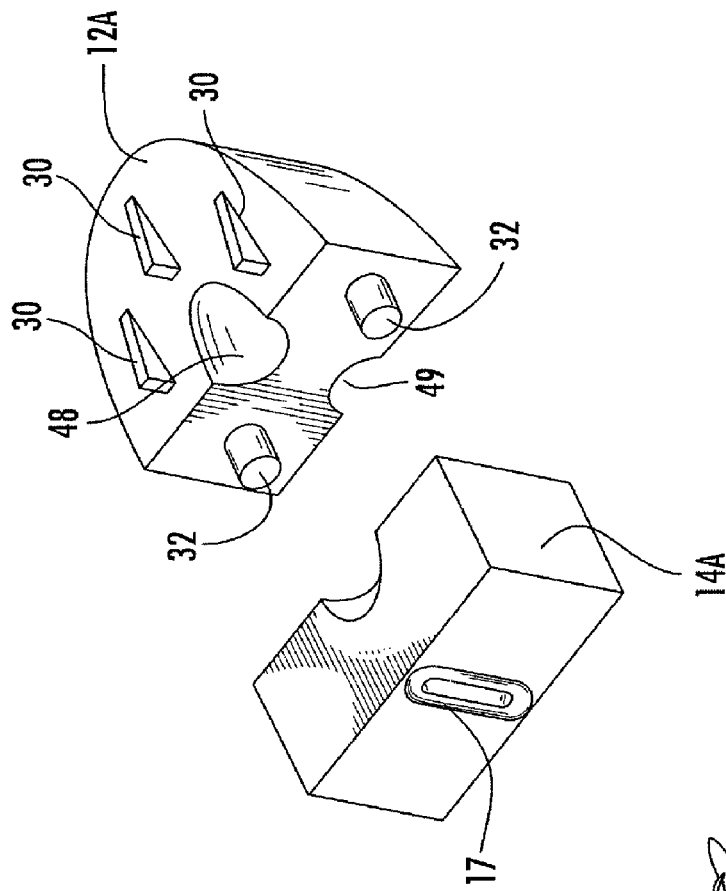
FIG. 3A is an illustrative embodiment of a biomechanical implant construct.
Figure 3A:
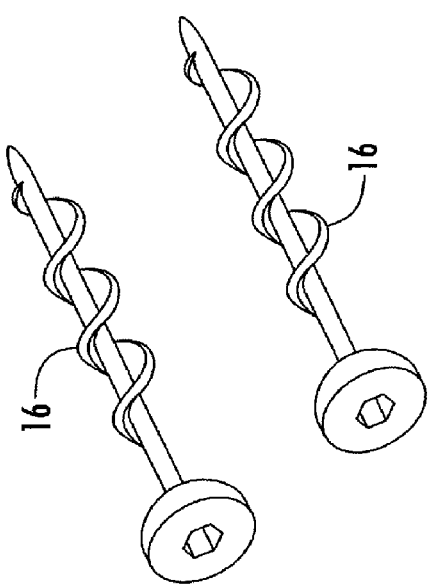
Figure 3B:
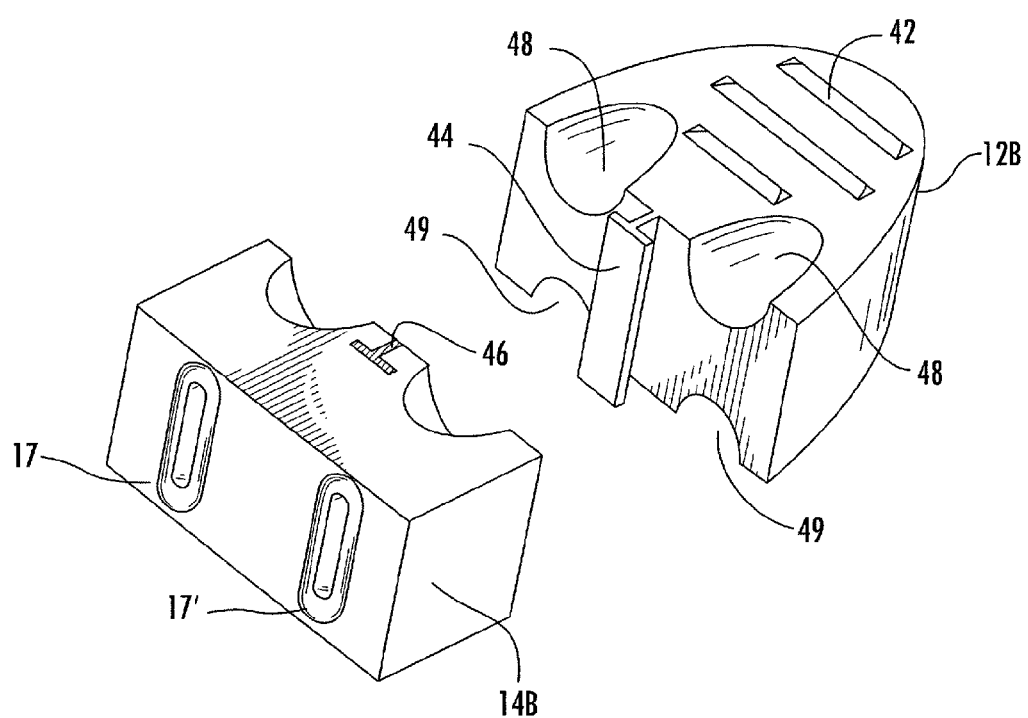
FIG. 3B is a further illustrative embodiment of a biomechanical implant construct.
Figure 3C:
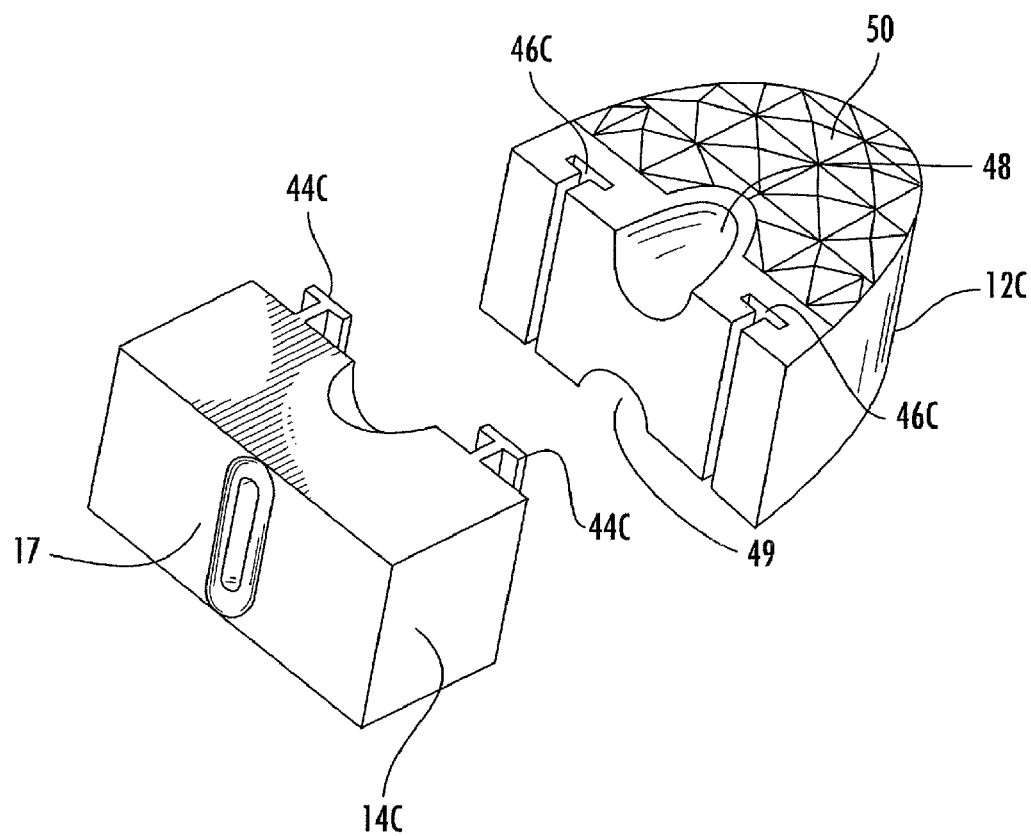
FIG. 3C is yet another illustrative embodiment of a biomechanical implant construct.

With reference to FIGS. 3A, 3B and 3C, alternative illustrative embodiments, in accordance with the inventive concept are illustrated. Such embodiments are for illustration purposes, and are not meant to limit the invention, as further equivalent alternative embodiments are contemplated.

Referring to FIG. 3A, implant 12A shows one illustrative embodiment of a biomechanical implant element wherein the element includes one or more keel-like members 30. The attachment of plate 14A and implant 12A is accomplished via pins 32, which are designed for frictional insertion and engagement with mating recesses (not shown), in plate 14A. When positioned within the intervertebral space, fixation elements, e.g. screws 16, are inserted via access through-hole 17, and may follow the trajectory delineated by optional upper and lower guides 48 and 49 respectively.

Referring to FIG. 3B, implant 12B shows another illustrative embodiment of a biomechanical implant element wherein the element includes openings 42 for the insertion of bone graft material. The attachment of plate 14B and implant (graft/spacer) 12B is accomplished via coupling of male and female T-slot members 44 and 46. When positioned within the intervertebral space, fixation elements, e.g. screws 16 (not shown), are inserted via access through-holes 17 and 17', and may follow the trajectory delineated by optional upper and lower guides 48 and 49 respectively. It is noted that this embodiment illustrates plural access through holes 17 and 17', and when plate 14B is constructed from PEEK, the curvilinear through-hole engagement surface is formed from a metallic material, e.g. titanium, and inserted or molded into the PEEK implant to form a reinforced version of through-holes as illustrated at 17 and 17'.

Referring to FIG. 3C, implant 12C shows another illustrative embodiment of a biomechanical implant element wherein the element includes facets 50 for enhanced gripping of the adjacent vertebral bodies 18 and 20. The attachment of plate 14C and biomechanical implant 12C is illustratively accomplished via coupling of plural male and female T-slot members 44C and 46C. When positioned within the intervertebral space, fixation elements, e.g. screws 16 (not shown), are inserted via access through-hole 17, and may follow the trajectory delineated by optional upper and lower guides 48 and 49 respectively.

In a particular embodiment, the biomechanical spacer implant of the invention is adapted for insertion within an intervertebral space between a superior vertebral body and an inferior vertebral body and includes a first insertion end portion, a second end portion opposite the first end portion, a first lateral side portion, a second lateral side portion, an upper surface and a lower surface.

The particular surface shape and curvature, or taper in the anterior-posterior direction as well as between the lateral side surfaces will depend upon the location at which the spacer is intended to be inserted. The shape of the perimeter of the spacer can be modified for cervical applications, or for other areas such as in the lumbar or thoracic area of the spine.

Forms of attachment between the biomechanical implant element and the anterior instrumentation member are not limited to the mechanisms depicted. Furthermore, the number and position of access through-holes e.g. two, three, four or the like, is dictated by the particular patient's anatomy or other surgical considerations, and is also not intended to be limited by the type of attachment mechanism between the biomechanical implant and anterior instrumentation.

It is contemplated that the implant may include a series of teeth (FIG. 1, 19), knurling, ridges or similar projections, to aid in securing the implant to the vertebral endplates. It is also contemplated that the upper and/or lower surfaces of implant 12 may be smooth, having ridges (not shown) that run laterally with respect to the spacer, or ridges running from front to back.

It is further contemplated that the access through holes 17 provided in the plates may be threaded or smooth, and the screws or alternative bone fasteners inserted through the plate may have a head that also may be threaded or smooth. In this regard, and with reference to FIG. 20, the present invention contemplates an embodiment which incorporates the TIFIX technology disclosed by Wolter, in U.S. Pat. No. 6,322,562, wherein the bone screw may further include a preformed thread below the bone screw seat surface, the preformed thread deforming a portion of the passage hole below the seat surface of the connection carrier when the bone screw is screwed in so that a thread connection is formed between the bone screw thread and the connection carrier, the deformation being formed by rotating the bone screw at a certain angle to the connection carrier. In addition to use of bone screws, per se, such as disclosed by Wolter, the present invention further contemplates alternative embodiments wherein the preformed thread consists of a harder material than the deformable projection, wherein the bone screw or its casing is of a harder material than the connection carrier or the region to be deformed, wherein the casing region of the locking bolt has a lesser hardness than the bonemarrow nail at least in the region of the inner thread, wherein the connection carrier comprises a sensor for determining the force transmitted by the connection carrier between the bone ends and a transmitter for the telemetric transfer of the readings, and wherein the sensor and/or transmitter are integrated into a cavity of the connection carrier.

The implants described herein may be sized and configured for anterior, posterior or lateral approaches and insertion. In addition to the features shown the implants, spacers, and plate/spacer constructs may have threaded holes, slots or channels to mate with instruments to facilitate holding and inserting the implants.

To improve the anchoring of the bone fixation element in any of the illustrative embodiments contemplated by the present invention where the retention member is formed of a polymeric material, a metal sleeve with or without an internal thread, as illustrated in FIG. 3B, may be inserted in the access through hole 17. The intervertebral implant may also consist only partially of an x-ray transparent plastic and, in the region of the upper and lower guides (48,49) consist of a metal, such as titanium or a titanium alloy. Improved guidance and anchoring of the bone fixation elements may thereby be achieved. Further, the access through-holes may have a smooth internal wall, into which the threaded head or body of a metallic, longitudinal fixation element may cut or be molded.

Figure 4:
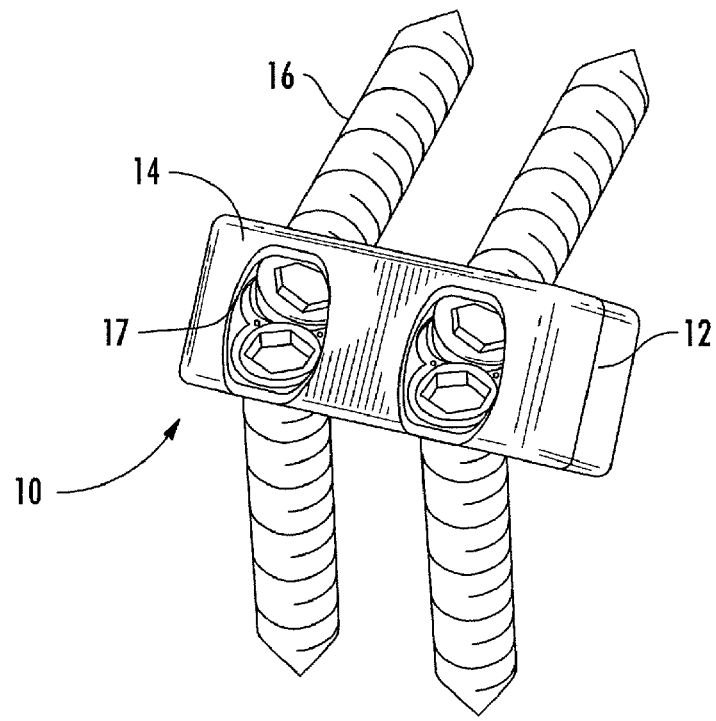
FIG. 4 illustrates a perspective view of a biomechanical implant and anterior instrumentation construct in accordance with the instant invention, in a vertically spaced configuration.

Now referring to FIG. 4, the biomechanical implant and anterior instrumentation construct, generally referred to by numeral 10, includes an implant member 12, and a retention member 14, illustrated as, albeit not limited to, a bone plate. Both biomechanical implant 12 and anterior instrumentation construct 14 may be formed of PEEK, titanium, titanium alloy, stainless steel, allograft bone or any other suitable, biocompatible material. Preferably retention member 14 is formed of metal or metal alloy and the spacer is formed of PEEK or other polymer, or alternatively bone or ceramic or radiolucent biocompatible material. Bone fixation elements 16, illustrated, albeit not limited to bone screws, may be formed of titanium, titanium alloy, stainless steel or other biocompatible materials. The bone fixation elements 16 may be in the form of a screw, a staple or nail, a fluted cannulated screw or nail with collapsible/deployable spurs which are deployed and thereby embedded within the bone upon insertion of a secondary nail or screw within the cannulated space, or similar elements. Furthermore, the implant 12 may include one or more openings (not shown) designed to receive bone graft material. Subsequent to insertion of the biomechanical implant and anterior instrumentation construct 10 within an intervertebral space (not illustrated), bone fixation elements, e.g. screws 16, are driven into the inferior and superior adjacent vertebral bodies, via an access through hole or borehole 17. Upon being fixated within said access hole 17, the elements 16 are in locking engagement with the retention member 14, and each other, so as to reduce or eliminate the possibility of loosening. In the vertical spaced orientation as shown, due to the single access hole design, the screws essentially reside in a single plane common to the superior and inferior vertebral bodies.

It is contemplated by the invention that each borehole 17 may include a single exit aperture or dual diverging exit apertures at the rear surface of the anterior instrumentation 14. The engagement seat of each aperture, whether integral with the assembly, or formed within a metallic insert that is subsequently inserted into the assembly, may include a spherical or semi-spherical dished and curvilinear seat for each fastener. This feature will enable variations in the choice of screw trajectory and increased face contact between the fixation elements and the plate or seat. In a preferred albeit non-limiting embodiment, the fastener element 16 will be formed with a spherical or semi-spherical head with a substantially flat upper surface. Such construction will allow the spherical surface of the second fastener, e.g. screw, to engage the top surface of the first screw regardless of trajectory of both screws, as the second screw is tightened and urged into frictional engagement with the first screw by contact with the dished and curvilinear engagement seat formed within the upper or entry surface of borehole 17. Such construction insures repeatable and reliable head-to-head contact independent of fastener trajectories.

Figure 5:
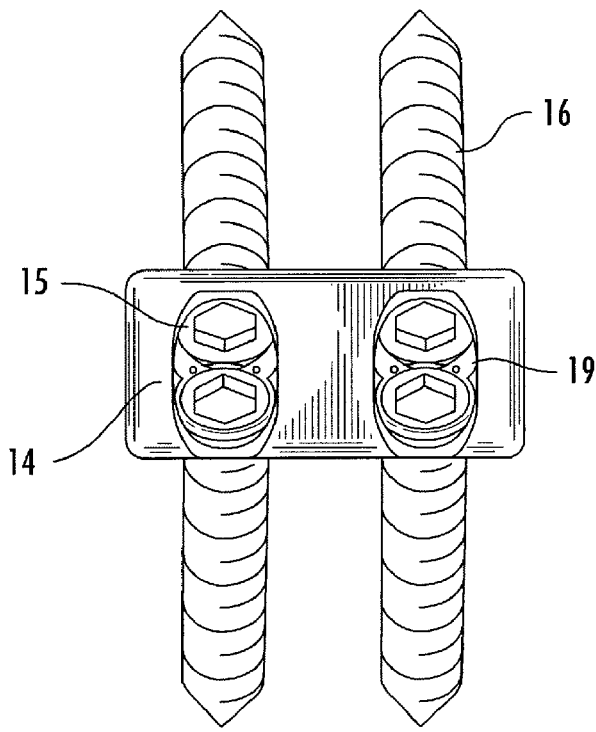
FIG. 5 illustrates a top-view of the biomechanical implant and anterior instrumentation construct of FIG. 4.

Now referring to FIG. 5, a top-view of the intervertebral implant assembly 10 of FIG. 4 is illustrated. This view best illustrates the bent open eight retention clip 15 as positioned within a prefabricated groove in borehole 17. In order to form a prefabricated and unitary assembly for simplified insertion during surgery, clip 15 is initially compressed by inserting a tool into holes 19 so as to enable the compressed clip to be inserted and thereby engage with reception grooves formed at the periphery of borehole 17. Subsequent to compression of the clip via holes 19 and insertion into borehole 17, the retention ring/clip 15 and retention member 14 form a unitary assembly. Each of the fixation elements 16 can be inserted individually in their respective apertures, and the retention ring 15 is designed to deflect so as to enable the heads of the fixation elements 16 to pass therethrough, and then return to its prior position to prevent the fixation element from falling out of borehole 17 should it become loosened.

Figure 6:
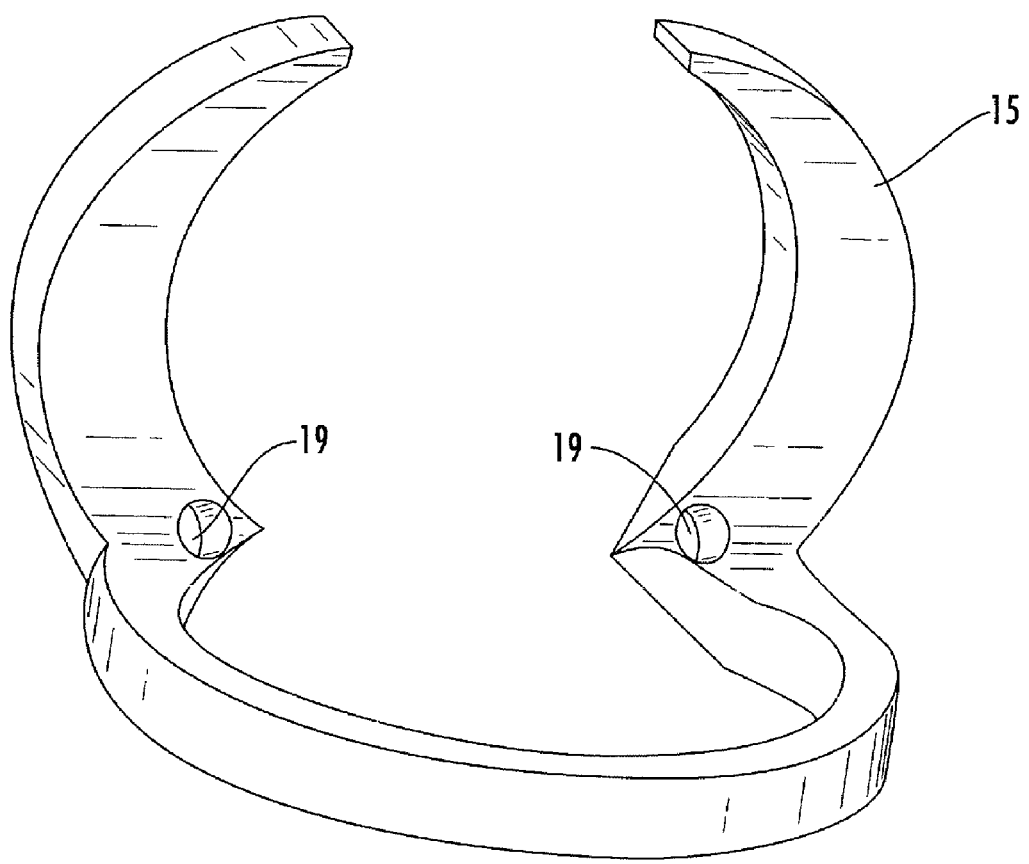
FIG. 6 illustrates a bent open eight screw retainer component for use in the biomechanical implant construct of FIGS. 4 and 5.

Referring to FIG. 6 the bent open eight retention clip 15 is more clearly illustrated. The bent configuration allows functionality in the vertical spaced orientation as illustrated, by providing a single clip which functions for both fixation elements.

Figure 7:
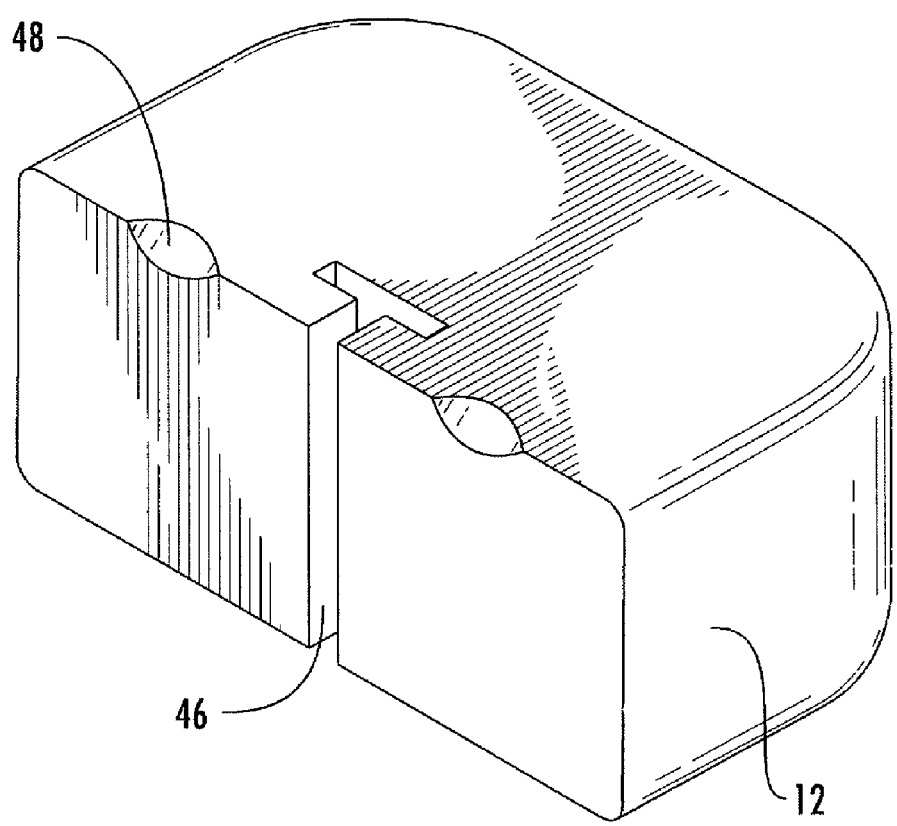
FIG. 7 is an illustrative embodiment of a biomechanical implant body alone.

Referring to FIG. 7 implant member 12 is an illustrative embodiment of an implant element. The element may contain openings (not shown here) for the insertion of bone graft material. The attachment of plate 14 and implant 12 is accomplished via coupling of male and female T-slot members 44 and 46 (more clearly illustrated in FIG. 9). When positioned within an intervertebral space, fixation elements, e.g. screws 16 (not shown), are inserted via access through-holes 17, and may follow the trajectory delineated by optional guides 48 and 49 respectively.

Figure 8:
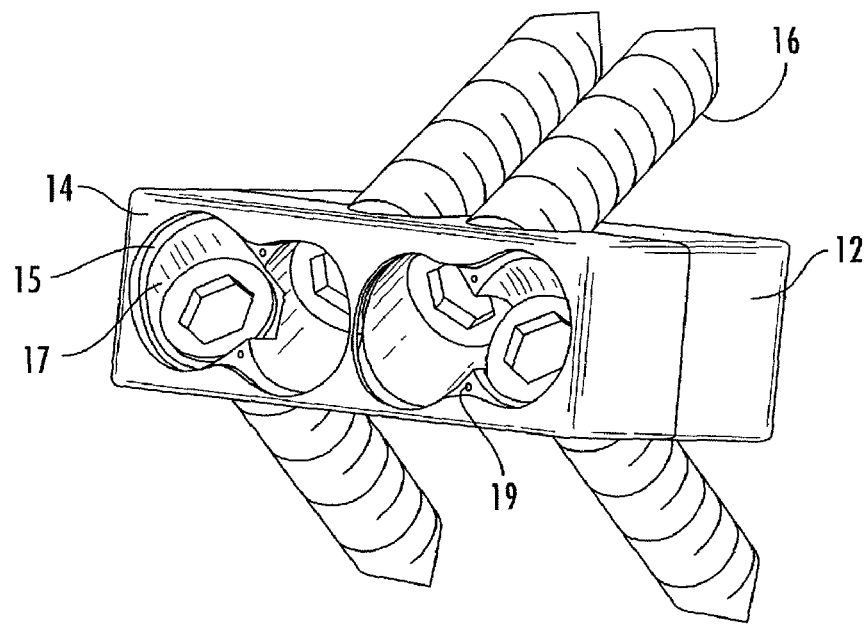
FIG. 8 illustrates a first perspective view of a biomechanical implant and anterior instrumentation construct in accordance with the instant invention, in a horizontally spaced configuration.

Referring to FIG. 8 illustrated herein is a first perspective view of a biomechanical implant and anterior instrumentation construct, in accordance with the instant invention, in a horizontally spaced configuration. Although the configuration of the boreholes and plates is slightly different between the vertically and horizontally spaced embodiments, the numbering has nevertheless been left consistent for ease of explanation. This is an alternative embodiment wherein, dependent upon the physiology and anatomy, it may be more desirable to position fixation elements 16 side by side, as opposed to vertically stacked. The functioning of the various elements is otherwise equivalent, except for the fact that the open eight screw retainer component 15, as illustrated in FIG. 10 is of a flat, rather than a bent, design.

Figure 9:
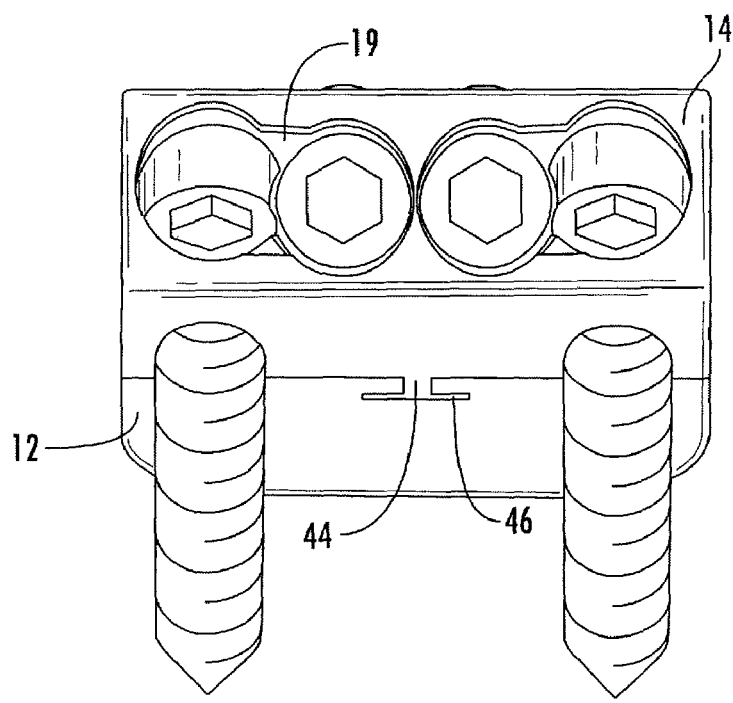
FIG. 9 illustrates a second perspective view of the biomechanical implant and anterior instrumentation construct of FIG. 8.

Referring to FIG. 9, a second perspective view of the biomechanical implant and anterior instrumentation construct of FIG. 8 is illustrated which more clearly depict the male/female T-slot configuration by which members 12 and 14 are assembled. It is stressed that this is merely one illustrative means of attachment of members 12 and 14 and any other functionally equivalent means of attachment are deemed to be within the purview of this invention.

Figure 10:
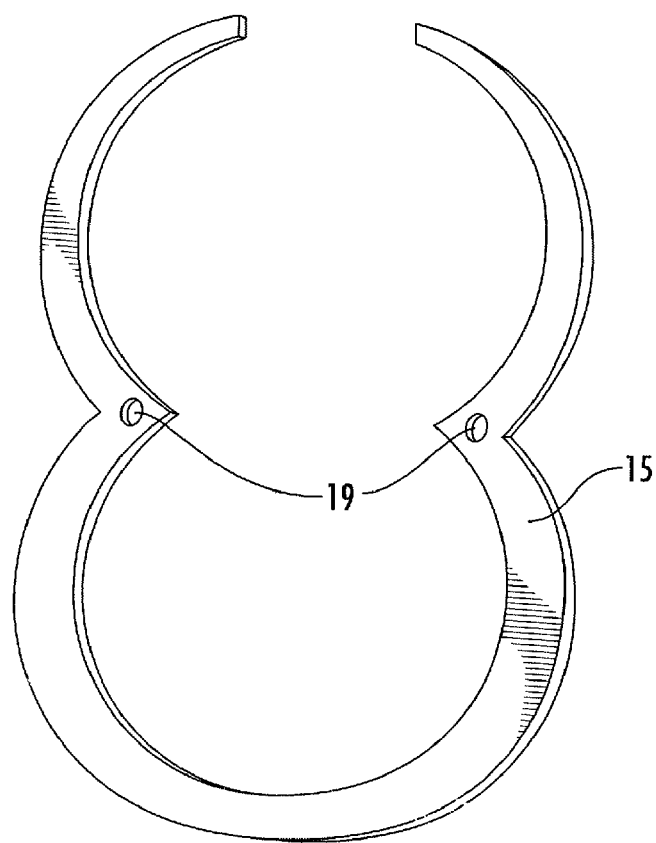
FIG. 10 illustrates a flat open eight screw retainer component for use in the intervertebral implant assembly of FIGS. 8 and 9.

Referring to FIG. 10, illustrated here is a flat open eight screw retainer component 15 for use in a biomechanical implant and anterior instrumentation construct of FIGS. 8 and 9. The functionality is equivalent to that of the bent design of FIG. 6 as previously outlined above.

Figure 11:
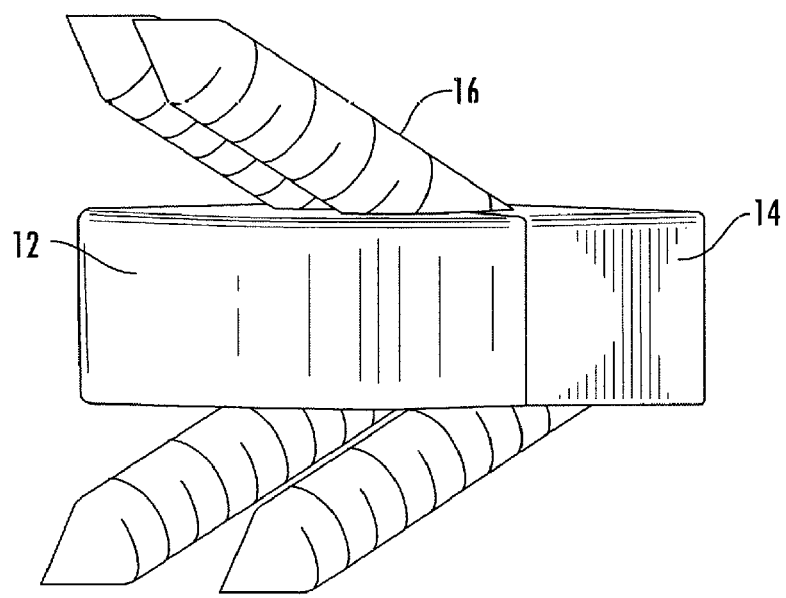
FIG. 11 illustrates an alternative view of the biomechanical implant and anterior instrumentation construct of FIGS. 8 and 9.

Referring to FIG. 11 an alternative view of the biomechanical implant and anterior instrumentation construct of FIGS. 8 and 9 is further illustrated.

Figure 12:
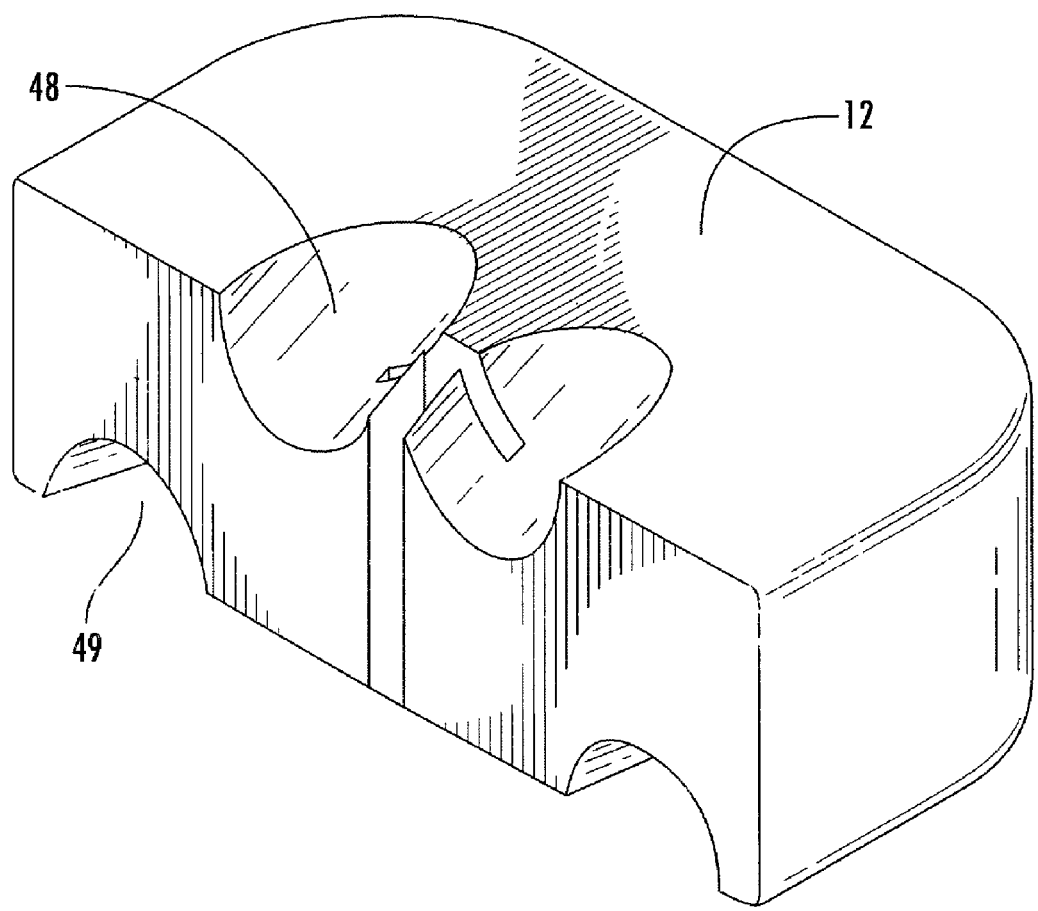
FIG. 12 is an illustrative embodiment of the biomechanical implant body alone.

Referring to FIG. 12, an illustrative embodiment of the intervertebral biomechanical implant member 12 is shown which illustrates the trajectory guiding elements 48 and 49, as they are positioned within the horizontally spaced configuration. Although a very basic illustration of implant member 12 is shown for ease of illustration, it is understood that the implant element 12 may include facets for enhanced gripping of the adjacent vertebral bodies. The particular surface shape and curvature, or taper in the anterior-posterior direction as well as between the lateral side surfaces will depend upon the location the spacer is intended to be inserted. The shape of the perimeter of the spacer can be modified for cervical applications, or for other areas such as in the lumbar or thoracic areas of the spine.

It is contemplated that the implant may include a series of teeth, knurling, ridges or similar projections, to aid in securing the implant to the vertebral endplates. It is also contemplated that the upper and/or lower surfaces of implant 12 may be smooth, having ridges (not shown) that run laterally with respect to the spacer, or ridges running from front to back.

It is reiterated that forms of attachment between the implant element 12 and the anterior instrumentation 14 are not limited to the mechanisms depicted. Furthermore, the number and position of access through-holes e.g. two, three, four or the like, is dictated by the particular patient's anatomy or other surgical considerations, and is also not intended to be limited by the type of attachment mechanism between the implant 12 and the biomechanical implant and anterior instrumentation construct 14.

As previously set forth, it is further contemplated that the access through holes 17 provided in all plates illustrated herein, may be threaded or smooth, and the fixation elements 16, such as screws or alternative bone fasteners inserted through the plate may have a head that also may be threaded or smooth.

All implants described herein may be sized and configured for anterior, posterior or lateral approaches and insertion. In addition to the features shown the implants, spacers, and plate/spacer constructs may have threaded holes, slots or channels to mate with instruments to facilitate holding and inserting the implants.

Figure 13:
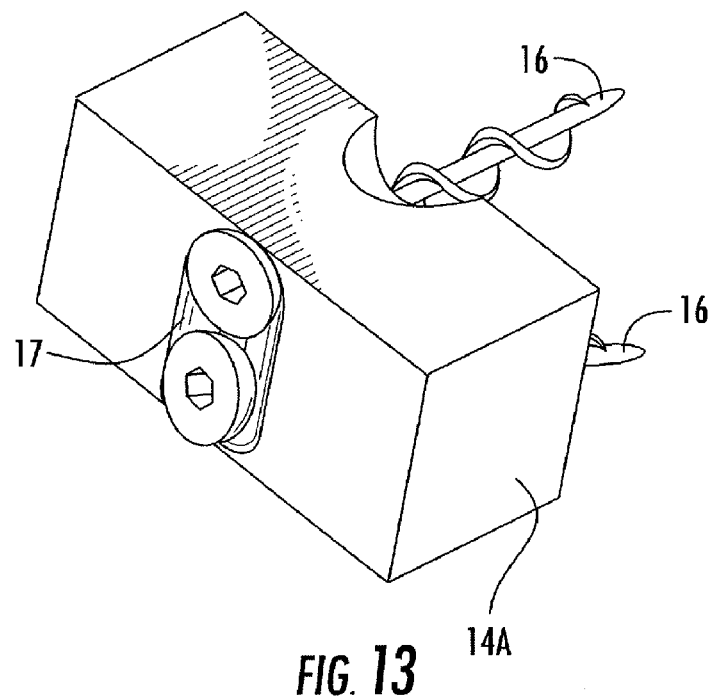
FIG. 13 illustrates the cooperation between the dished and curvilinear seat of the anterior instrumentation and the bone fastening elements upon tightening, to affect a locking engagement therebetween.
Figure 14:
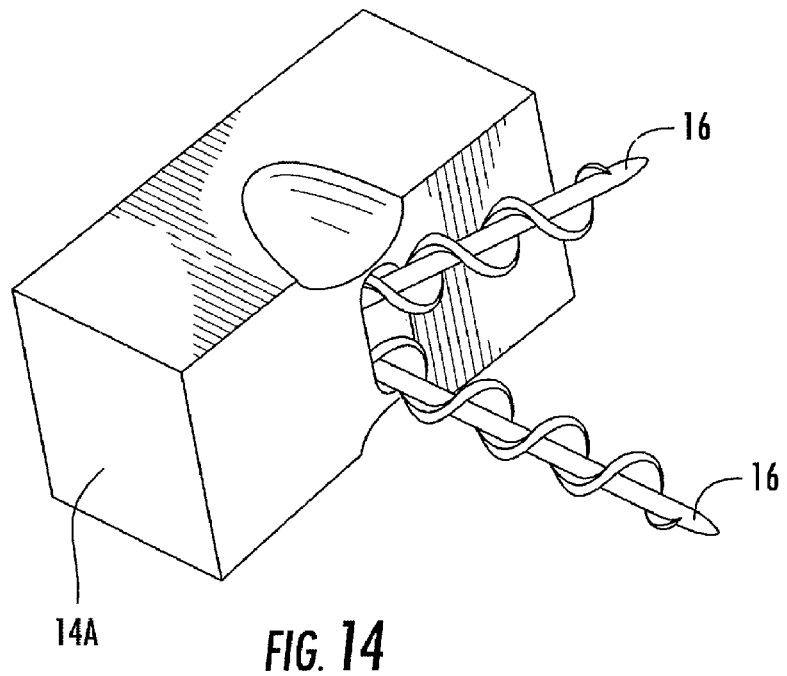
FIG. 14 illustrates a lower side view of the exiting of the bone fastening elements from the anterior instrumentation of the implant of FIG. 13.
Figure 15A:
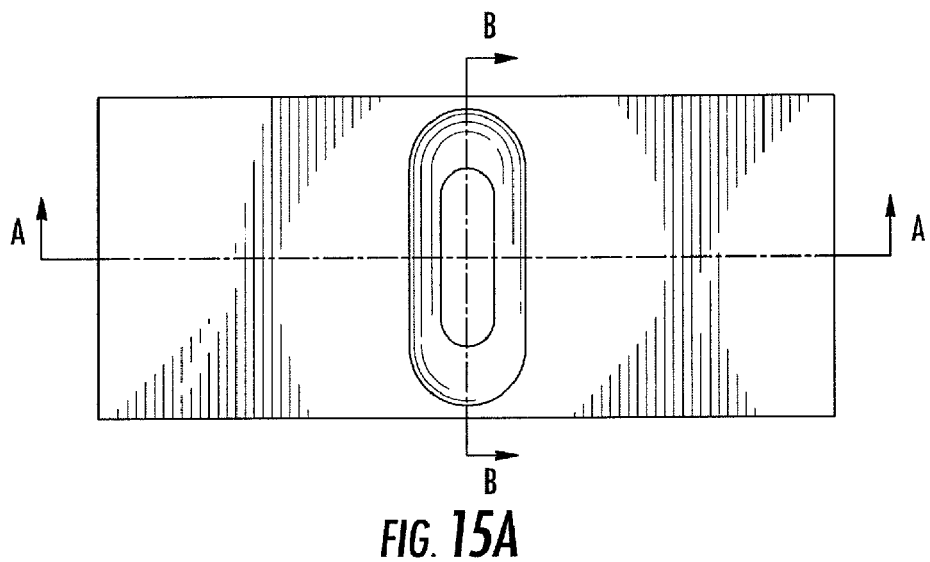
FIG. 15A is a top view of an elongated borehole slot surrounded by an arcuate and curvilinear seat formed within an anterior instrumentation.
Figure 15B:
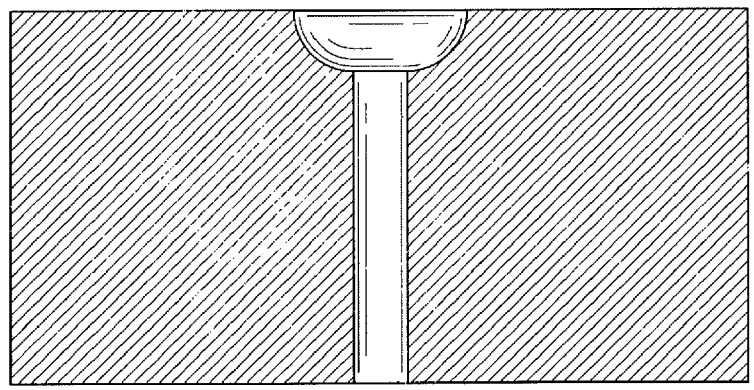
FIG. 15B is a cross-sectional view of FIG. 15A along line A-A.
Figure 15C:
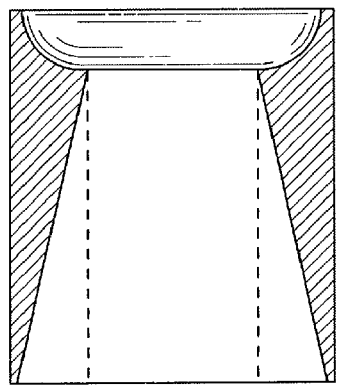
FIG. 15C is a cross-sectional view of FIG. 15A along line B-B.

Referring to FIG. 13 the cooperation between the dished and curvilinear seat illustrated within the entry area of borehole 17 is illustrated, showing the cooperation between the seat area and the heads of the bone fastening elements 16 upon tightening, to affect a locking engagement therebetween;

With reference to FIG. 14 illustrates, a view of the lower side of instrumentation plate 14A shows divergent exiting of the bone fastening elements 16 toward the inferior and superior vertebral bodies, from the anterior instrumentation of the implant of FIG. 13;

Now referring to FIG. 15A is an illustrative embodiment showing a top view of an elongated borehole slot 17B surrounded by an arcuate and dished curvilinear seat 17A formed within the instrumentation plate 14A;

Referring to FIG. 15B, illustrated herein is a cross-sectional view of FIG. 15A along line A-A, showing the dished and curvilinear shape of seat 17A, which will cooperate with relatively congruent shaped screw heads provided to bone screws 16 (not shown here for clarity), in order to enhance the cooperation between these elements during the fixation process, so as to urge the screw heads and engagement seat into a locking frictional engagement;

With further reference to FIG. 15C, shown here is a cross-sectional view of FIG. 15A along line B-B, which illustrates the exit aperture 17C, which enables the discretion in angular placement of the fixation elements 16, into the vertebral bodies, as desired by the surgeon.

Figure 16:
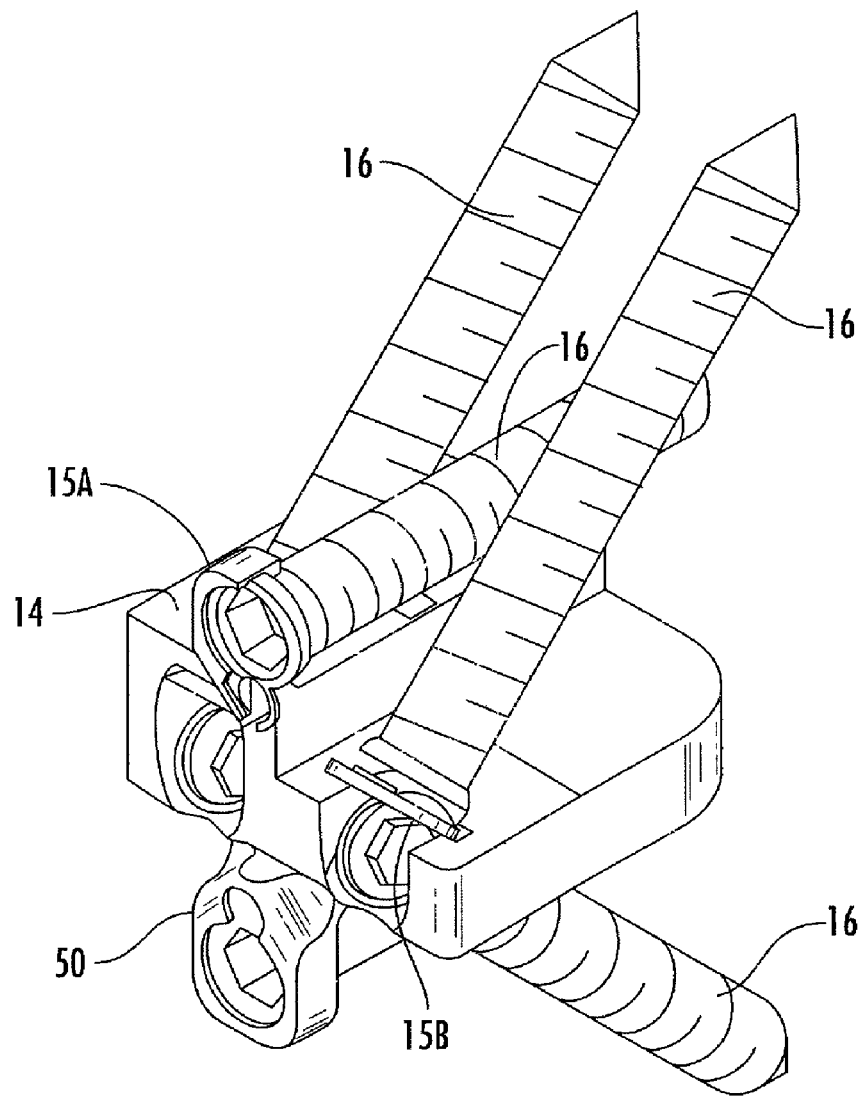
FIG. 16 is a front perspective view, partially in section, of a vertically spaced biomechanical implant assembly further including anchoring tabs for attachment to the anterior cortical vertebral surfaces.

Referring now to FIG. 16, is a front perspective view is shown, partially in section, of a vertically spaced biomechanical implant assembly 12, with stabilizing anterior instrumentation 14, further including anchoring tabs 50 for attachment to the anterior cortical vertebral surfaces. This embodiment provides the surgeon with the utility of attachment of additional stabilization through the anterior cortical bone surfaces by insertion of a fastener element 16, through tab 50, which is retained by deflectable retention element 15A, which is a further variation on the "open-eight" retention element technology illustrated in earlier embodiments. The partial sectional view affords an alternative view of the relationship of bent retention element 15B, within a reception groove formed in plate 14, in this vertically oriented configuration.

Figure 17:
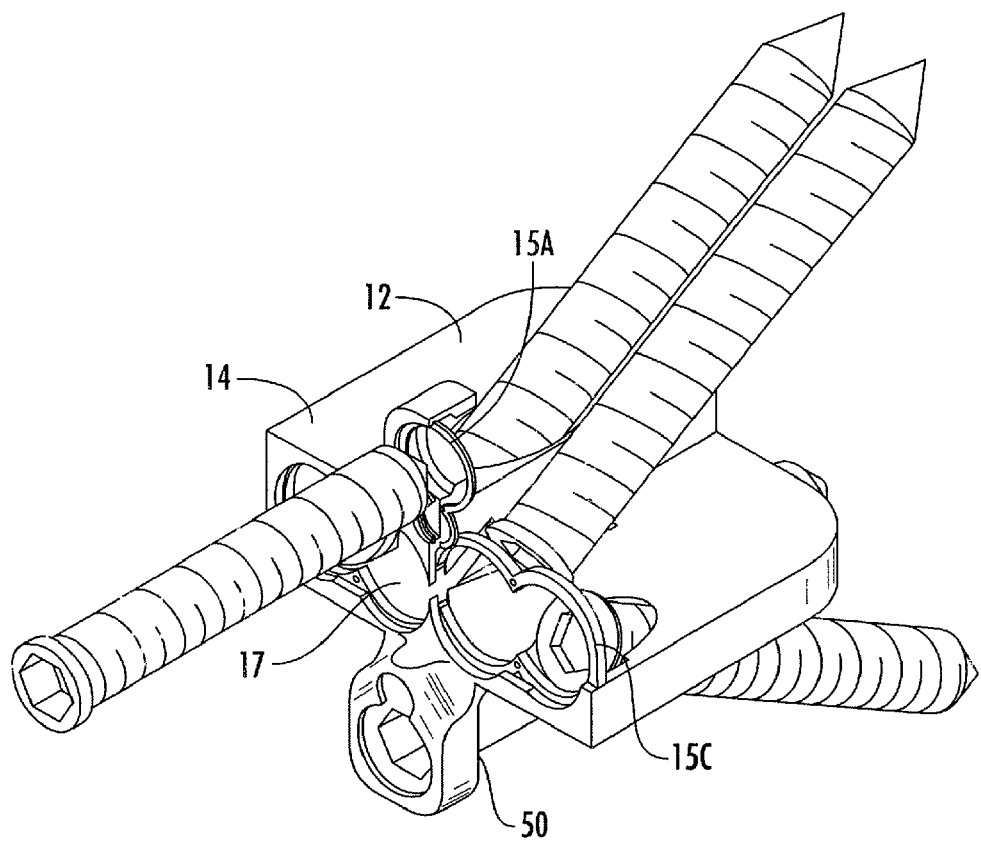
FIG. 17 is a front perspective view, partially in section, of a horizontally spaced biomechanical implant assembly further including anchoring tabs for attachment to the anterior cortical vertebral surfaces.

With reference to FIG. 17, a front perspective view, partially in section, of a horizontally spaced biomechanical implant assembly further including anchoring tabs for attachment to the anterior cortical vertebral surfaces is shown. This assemblage is essentially the same as that described in FIG. 16 above, save for the fact that it is configured to be horizontally oriented so as to provide an alternate bone screw placement. The flat open eight retention member 15C is illustrated placed within a retention groove formed with instrumentation plate 14 for retention thereof.

Figure 18:
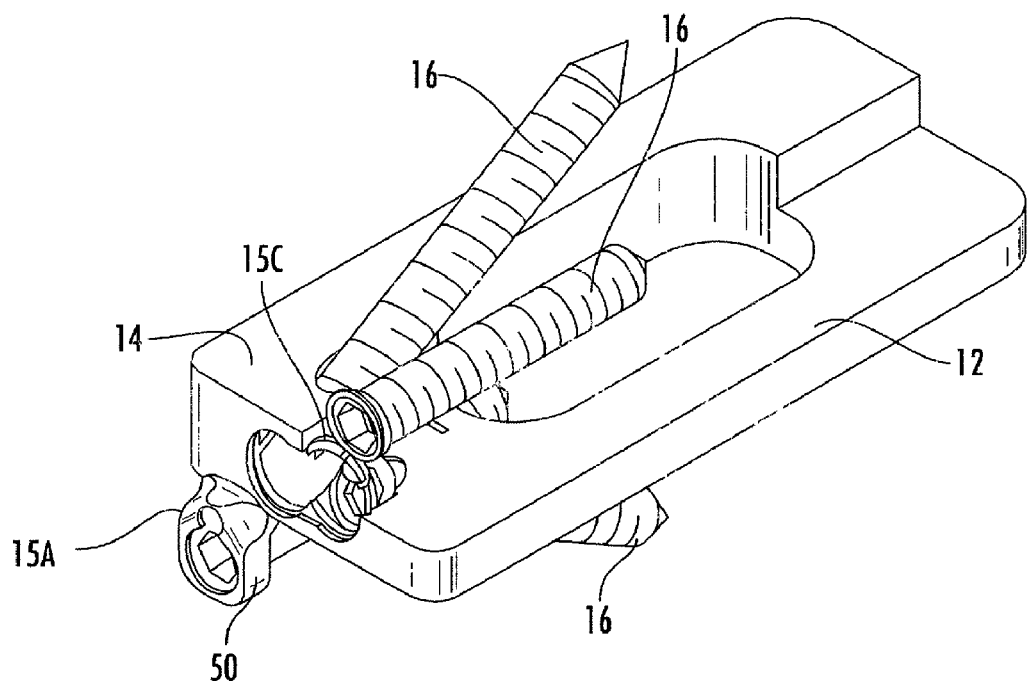
FIG. 18 is a front perspective view, partially in section, of a horizontally spaced biomechanical implant assembly for lateral insertion, including anchoring tabs for attachment to the lateral cortical vertebral surfaces.

Referring to FIG. 18, shown herein is a front perspective view, partially in section, of a horizontally spaced biomechanical implant assembly, as illustrated in FIG. 17, however configured for lateral insertion, including anchoring tabs for attachment to the lateral cortical vertebral surfaces.

Figure 19:
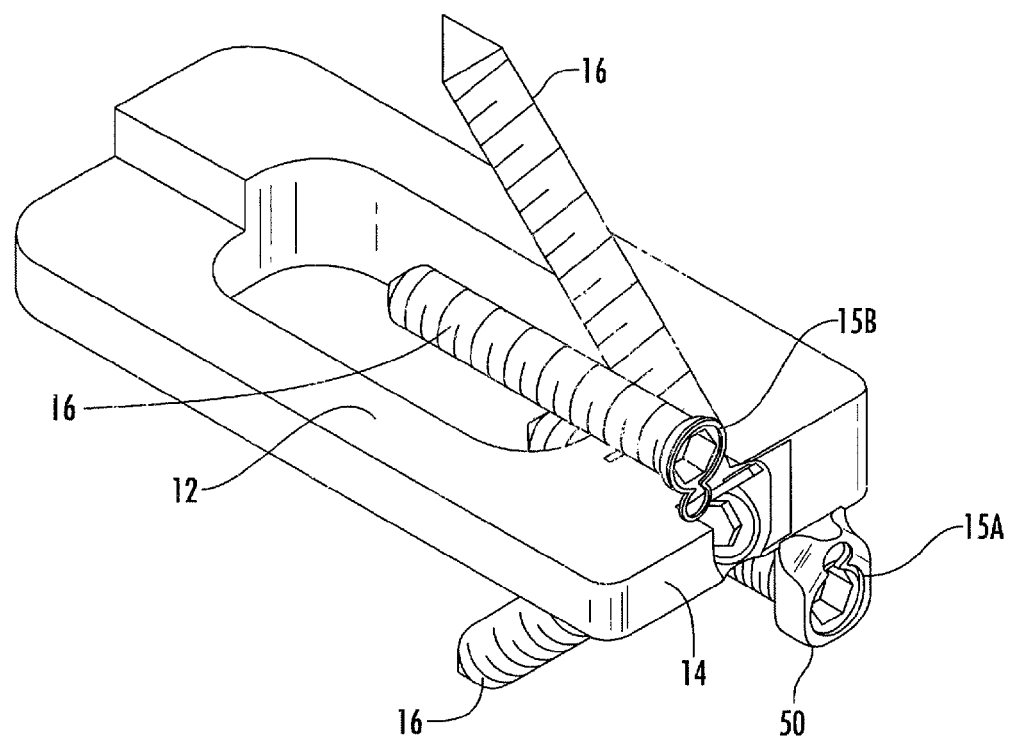
FIG. 19 is a front perspective view, partially in section, of a vertically spaced biomechanical implant assembly for lateral insertion, including anchoring tabs for attachment to the lateral cortical vertebral surfaces.

With further reference to FIG. 19, a front perspective view, partially in section, of a vertically spaced biomechanical implant assembly for lateral insertion, including anchoring tabs for attachment to the lateral cortical vertebral surfaces is also shown.

Figure 20:
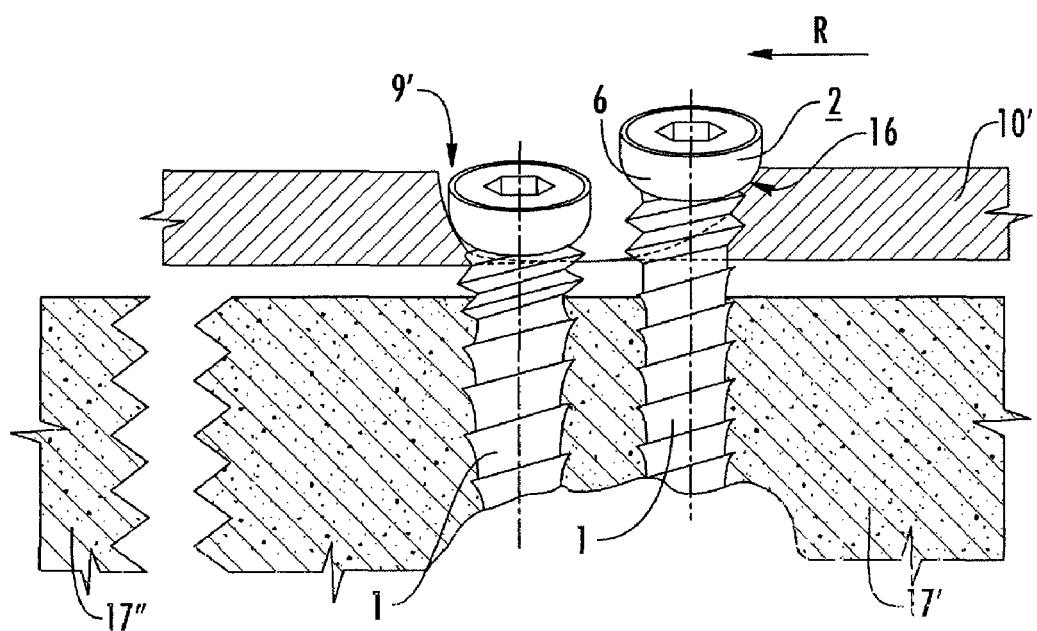
FIG. 20 is a cross-sectional view of a prior art TIFIX plate and screw combination.

FIG. 20 is a cross-sectional view of a prior art TIFIX plate and screw combination. It is contemplated that any of the herein illustrated and referenced embodiments could be modified to contain the TIFIX technology. Such incorporation might include merely selecting the relative hardnesses of the materials used in the fixation elements 16 and plates 14, 14A, etc. so as to provide thread forming ability and autogenic locking, in the manner described by Wolter '562. Additionally, it is further contemplated to modify the bone fixation elements 16, to include secondary threads for locking into the plate as shown in prior art FIG. 20 from the Wolter '562 patent.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A stabilizing bone plate useful in an interbody fusion system for stabilizing a biomechanical spinal implant comprising:
   a bone plate having a left side surface and a right side surface, a top surface and a bottom surface, a first upper surface and a second lower surface, with a distance between said first upper surface and said second lower surface defining a thickness of said plate, a horizontal middle plane between the first upper surface and the second lower surface and a plurality of boreholes suitable for accommodating longitudinal fixation elements extending through said thickness of said plate;
   wherein each of said boreholes has an elongated slot located at or near said horizontal middle plane, and surrounded by arcuate and dished curvilinear sidewalls which form an engagement seat extending from said elongated slot to said first upper surface for receiving at least two bone fixation elements therein, each of said bone fixation elements having a screw head that enters into locking engagement with at least one adjacent screw head to minimize movement of said bone fixation elements, and a diverging outlet portion extending from said elongated slot toward said second lower surface, said divergent outlet being adapted to provide a range of angulation of each said fixation elements;
   whereby each of said fixation elements is individually positionable within both an inferior and superior vertebral body associated with said interbody fusion system.

2. The bone plate of claim 1 further including a screw retainer component comprising a resilient member constructed and arranged for insertion within a reception groove therefore adjacent the intersection of said borehole and said first upper surface;
   whereby said resilient member is adapted to be deflected to allow each said fixation element to be inserted into said borehole, and is further adapted to return to is original position subsequent to passage of said fixation elements;
   wherein a loosened or broken fixation element is retained within said borehole.

3. The bone plate in accordance with claim 2 wherein said resilient member is in the form of an open figure eight.

4. The stabilizing bone plate of claim 1 comprised of a material selected from the group consisting of poly ether ether ketone (PEEK), titanium, a titanium alloy, stainless steel, allograft bone, plastic, ceramic and combinations thereof.

5. The stabilizing plate of claim 4, wherein said engagement seat is a metallic insert.

6. The stabilizing plate of claim 5, wherein said engagement seat is a metallic insert.

7. The bone plate of claim 1 further including at least one anchoring tab positioned above and in juxtaposed relation to a plane defined by said first upper surface of said bone plate.

8. An interbody fusion system comprising in combination:
   a biomechanical spacer implant adapted for insertion within an intervertebral space between a superior vertebral body and an inferior vertebral body, said implant having a first insertion end portion, a second end portion opposite the first end portion, a first lateral side portion, a second lateral side portion, an upper surface and a lower surface; and
   a bone plate having a left side surface and a right side surface, a top surface and a bottom surface, a first upper surface and a second lower surface, with a distance between said first upper surface and said second lower surface defining a thickness of said plate, a horizontal middle plane between the first upper surface and the second lower surface and a plurality of boreholes suitable for accommodating longitudinal fixation elements extending through said thickness of said plate, wherein each of said boreholes has an elongated slot located at or near said horizontal middle plane, and surrounded by arcuate and dished curvilinear sidewalls which form an engagement seat extending from said elongated slot to said first upper surface for receiving at least two bone fixation elements therein, each of said bone fixation elements having a screw head, and a diverging outlet portion extending from said elongated slot toward said second lower surface, said divergent outlet being adapted to provide a range of angulation of each said fixation elements, whereby each of said fixation elements is individually positionable within both an inferior and superior vertebral body associated with said interbody fusion system,
   wherein, upon engagement with the engagement seat, each screw head frictionally locks with an adjacent screw head to minimize disengagement of the at least two bone fixation elements and the engagement seat,
   wherein the at least two bone fixation elements are adapted for cooperating with said bone plate thereby securing said bone plate to said superior and inferior vertebral bodies.

9. The interbody fusion system of claim 8, wherein said biomechanical spacer implant further contains at least one hollow area adapted for holding bone growth promoting material.

10. The interbody fusion system of claim 8, wherein said fixation elements and said borehole cooperate to allow for angular motion of said bone screws relative to the implant.

11. The interbody fusion system of claim 8, wherein said fixation elements are sized and configured for use in the cervical spine.

12. The interbody fusion system of claim 8, wherein said fixation elements are sized and configured for use in the lumbar spine.

13. The interbody fusion system of claim 8, wherein said fixation elements are sized and configured for use in the anterior, posterior or lateral aspect of the spine.

14. The interbody fusion system of claim 8, wherein each of said upper and lower surfaces have at least one bone engaging projection thereon.

15. The interbody fusion system of claim 8, wherein said projection is a fin, a spike, a keel, a ridge, knurling, or a combination thereof.

16. The interbody fusion system of claim 8, wherein said biomechanical implant and said bone plate are adapted to form a unitary construct prior to insertion within an intervertebral space.

17. The interbody fusion system of claim 8, wherein said implant comprises an artificial material.

18. The interbody fusion system of claim 8, wherein said implant is made of an artificial material that is stronger than bone.

19. The interbody fusion system of claim 8, wherein said implant is made of an artificial material that is harder than bone.

20. The interbody fusion system of claim 8, wherein said implant comprises bone.

21. The interbody fusion system of claim 8, wherein said implant comprises bone growth promoting material.

22. The interbody fusion system of claim 21, wherein said bone growth promoting material is selected from one of bone morphogenetic protein, hydroxyapatite, and genes coding for the production of bone.

23. The interbody fusion system of claim 8, wherein said implant is treated with a bone growth promoting substance.

24. The interbody fusion system of claim 8, wherein said implant is a source of osteogenesis.

25. The interbody fusion system of claim 8, wherein said implant is formed of a porous material.

26. The interbody fusion system of claim 8, in combination with a chemical substance to inhibit scar formation.

27. The interbody fusion system of claim 8, in combination with a fusion promoting substance.

28. The interbody fusion system of claim 27, wherein said fusion promoting substance includes at least one of bone, bone morphogenetic protein, hydroxyapatite, and genetic materials coding for the production of bone.

29. The stabilizing bone plate of claim 8 comprised of a material selected from the group consisting of poly ether ether ketone (PEEK), titanium, a titanium alloy, stainless steel, allograft bone, plastic, ceramic and combinations thereof.

30. The interbody fusion system of claim 8 wherein said fixation elements are selected from the group consisting of a screw, a staple, a nail, a fluted cannulated screw and combinations thereof.

31. The interbody fusion system of claim 8 wherein materials selected for the fixation elements and bone plate are selected to be of differing hardness.

32. The interbody fusion system of claim 8 wherein said implant comprises a material selected from the group consisting of a material having an elasticity equal to, greater than or less than bone.

33. The bone plate of claim 8 further including at least one anchoring tab positioned above and in juxtaposed relation to a plane defined by said first upper surface of said bone plate.

\* \* \* \* \*